(12) United States Patent
Holzner et al.

(10) Patent No.: US 7,689,308 B2
(45) Date of Patent: Mar. 30, 2010

(54) METHOD, COMPUTER-READABLE MEDIUM, AND COMPUTER PROGRAM, CONCERNING THE MANUFACTURE OF DENTAL PROSTHESES AFTER BREAKAGE OF INITIAL PROSTHESES

(75) Inventors: Stephan Holzner, Hohenschäftlarn (DE); Gerhard Weber, Inning/Ammersee (DE)

(73) Assignee: Institut Straumann AG, Basel (CH)

( * ) Notice: Subject to any disclaimer, the term of this patent is extended or adjusted under 35 U.S.C. 154(b) by 431 days.

(21) Appl. No.: 11/486,979

(22) Filed: Jul. 13, 2006

(65) Prior Publication Data

US 2007/0050074 A1 Mar. 1, 2007

(30) Foreign Application Priority Data

Jul. 28, 2005 (DE) .................. 10 2005 035 475

(51) Int. Cl.
*G06F 19/00* (2006.01)
*A61C 13/00* (2006.01)

(52) U.S. Cl. ...................... 700/97; 433/201.1

(58) Field of Classification Search ............ 700/95–98, 700/117, 118; 433/167, 201.1, 202.1
See application file for complete search history.

(56) References Cited

U.S. PATENT DOCUMENTS

| | | | | |
|---|---|---|---|---|
| 4,742,473 | A * | 5/1988 | Shugar et al. ............... 715/821 |
| 5,131,844 | A * | 7/1992 | Marinaccio et al. .......... 433/72 |
| 6,109,919 | A | 8/2000 | Hansson |
| 6,739,870 | B2 * | 5/2004 | Lai et al. .................... 433/24 |
| 6,835,066 | B2 | 12/2004 | Iiyama et al. |
| 6,881,229 | B2 * | 4/2005 | Khandkar et al. ......... 623/23.56 |
| 7,092,784 | B1 * | 8/2006 | Simkins .................... 700/163 |
| 7,134,874 | B2 * | 11/2006 | Chishti et al. ................ 433/24 |
| 7,241,142 | B2 * | 7/2007 | Abolfathi et al. ............. 433/24 |
| 7,320,592 | B2 * | 1/2008 | Chishti et al. ................ 433/24 |
| 2004/0019382 | A1 * | 1/2004 | Amirouche et al. ....... 623/18.11 |
| 2005/0003329 | A1 | 1/2005 | Lehmann et al. |
| 2005/0043809 | A1 * | 2/2005 | Ryd ........................ 623/20.32 |
| 2005/0143967 | A1 * | 6/2005 | Holberg ........................ 703/6 |

(Continued)

FOREIGN PATENT DOCUMENTS

DE 10203665 11/2002

(Continued)

OTHER PUBLICATIONS

Hojjatie et al., "Three-Dimensional Finite Element Analysis of Glass-Ceramic Dental Crowns," J. Biomech., 23(11):1157-1166 (1990).*

(Continued)

*Primary Examiner*—Maria N. Von Buhr
(74) *Attorney, Agent, or Firm*—IP Strategies

(57) ABSTRACT

The invention relates to the examination of a dental prosthesis, wherein the dental prosthesis is examined with finite element methods. Furthermore, the invention relates to the automated manufacture of a dental prosthesis, wherein the shape of a remaining tooth area is directly determined on the basis of the remaining tooth area itself. Furthermore, the invention relates to a method, wherein manufacturing data (milling data) which have been created with a system for calculating manufacturing data (system for calculating milling data) are optionally forwarded to one or another manufacturing machine (milling machine) at different locations.

12 Claims, 23 Drawing Sheets

U.S. PATENT DOCUMENTS

| | | | |
|---|---|---|---|
| 2005/0192835 A1* | 9/2005 | Kuo et al. | 705/2 |
| 2006/0098008 A1* | 5/2006 | Holberg | 345/420 |
| 2006/0127848 A1* | 6/2006 | Sogo et al. | 433/173 |
| 2006/0131770 A1* | 6/2006 | Dierkes et al. | 264/16 |
| 2006/0257815 A1* | 11/2006 | De Dominicis | 433/24 |
| 2007/0015110 A1* | 1/2007 | Zhang et al. | 433/173 |

FOREIGN PATENT DOCUMENTS

| | | |
|---|---|---|
| DE | 10202515 | 8/2003 |
| DE | 10313690 | 11/2004 |
| EP | 1658825 | 5/2006 |
| WO | WO-2004/084756 | 10/2004 |

OTHER PUBLICATIONS

Futterling et al., "Automated Finite Element Modeling of a Human Mandible with Dental Implants," WSCG '98 -Conference Program, retrieved from the Internet: <http://wscg.zcu.cz/wscg98/papers98/Strasser.sub.--98.pdf>- ; 8 pages.*

Felton et al. "A computerized analysis of the shape and stability of manibular arch form," Am. Journal of Orthodontics and Dentofacial Orthopedics, vol. 92, No. 6 (Dec. 1987), pp. 478-483.*

Duret et al., "CAD/CAM Imaging in Dentistry," Current Opinion in Dentistry, vol. 1 (1991), pp. 150-154.*

Duret et al., "CAD-CAM in Dentistry," Journal of the American Dental Association, vol. 117 (Nov. 1988), pp. 715-720.*

Begole et al., "A Computer System for the Analysis of Dental Casts," The Angle Orthodontist, vol. 51, No. 3 (Jul. 1981), pp. 253-259.*

C. Rubin et al., "Stress Analysis of the Human Tooth using a Three-dimensional Finite Element Model", J. Dental Research, 62(2):82-86, Feb. 1983.*

* cited by examiner

METHOD, COMPUTER-READABLE MEDIUM, AND COMPUTER PROGRAM, CONCERNING THE MANUFACTURE OF DENTAL PROSTHESES AFTER BREAKAGE OF INITIAL PROSTHESES

BACKGROUND OF THE INVENTION

The invention relates to a method, a computer, a machine-readable medium, and a computer program with program code means by which a data record representing a dental prosthesis can be examined.

Further, the invention relates to a method and a system for the manufacture of a dental prosthesis, wherein a data record for a dental prosthesis is created and transmitted to a production system on the basis of a data record representing a remaining tooth area.

Furthermore, the invention relates to two methods and two systems for the manufacture of a dental prosthesis as well as a method for examining a dental prosthesis data record, a computer, a machine-readable medium, and a computer program concerning the examination of a dental prosthesis data record. These objects relate to the treatment of manufacturing data (e. g. milling data) as they are employed for the manufacture of dental prostheses.

Furthermore, the invention relates to two methods and two systems for creating dental prosthesis data records.

From WO 02/39056 A1, it is known to digitally detect the shapes of remaining tooth areas by means of patterns and to generate the shapes of dental prostheses on the basis thereof with the aid of software. In the process, data records representing a dental prosthesis are created which can subsequently be used when the dental prostheses are manufactured, for example by milling.

BRIEF SUMMARY OF THE INVENTION

It is an object of the present invention to improve the dental prostheses which can be manufactured by this procedure.

It is another object of the present invention to facilitate or accelerate the manufacture of dental prostheses.

It is another object of the present invention to integrate as optimally as possible existing appliances into the manufacture of dental prostheses.

It is another object of the present invention to permit the user the modeling of dental prostheses with means as simple as possible.

For improving the dental prostheses, it is suggested to examine the data records of the dental prostheses with finite element methods. With these methods, very diverse properties of the dental prostheses can be examined or else simulated. For example, the breaking strength of the dental prosthesis or the stability of a dental prosthesis during production etc. can be examined.

In application, dental prostheses underlie strong forces, for example, during chewing. In the process, the dental prosthesis is subjected to the pressure between upper and lower jaws. Therefore, in the examination of the data record, the data record of the remaining tooth area onto which the dental prosthesis is to be fitted and/or the data of the opposite tooth area (i.e. the upper jaw if the dental prosthesis is intended for the lower jaw, or vice versa, respectively) are advantageously considered. However, an examination without these data is also possible if, for example, any kind of force onto the dental prosthesis is simulated with predetermined limits. In the process, one can examine whether the dental prosthesis can deal with these forces.

A dental prosthesis is subjected to certain forces even during production, while it is, for example, manufactured by milling it out of a blank with a cutter head. The stability of the dental prosthesis for the production process can also be examined with finite element methods. Here, it has to be considered that the forces during production might be smaller than those in application, that, however, the milling material sometimes is raw ceramic material which is essentially more brittle compared to fired ceramic material.

In an advantageous operation, the result of the examination is filed for documentation purposes. Depending on the result of the examination, the data record of the dental prosthesis can be modified to achieve a sufficiently high and desired breaking strength.

The examination of the data record can be performed before as well as after the manufacture of the dental prosthesis. The performance beforehand has the advantage that the dental prosthesis can be possibly manufactured in a modified manner. On the other hand, an examination is possibly only necessary when the dental prosthesis is already broken and one has to determine why it is broken.

If the dental prosthesis is broken or if the examination of the dental prosthesis shows that it can be easily broken, a dental prosthesis data record is created which was preferably automatically changed such that the breaking strength was increased at the point of break. This can be performed, for example, by correspondingly increasing the wall thickness, by additional or thicker webs or the like. Moreover, the dental prosthesis of the new dental prosthesis data record is preferably manufactured directly. The new dental prosthesis data record can again be examined for its breaking strength. Here, with a repeating iteration method (breaking strength test, change of the dental prosthesis data record), a dental prosthesis data record can be obtained which corresponds to an optimized dental prosthesis.

Moreover, if only after the manufacture of the dental prosthesis the breaking strength is possibly doubted, the examinations with respect to the breaking strength can be performed in order to prove that the dental prosthesis can meet possible requirements.

Here, it is advantageous to graphically represent the tensions and/or forces and/or pressures that can lead to breaking, for example with colors, shades of gray, etc. These tensions, forces and/or pressures are established with the finite element method. This graphical representation as a rule permits a good possibility of judging the breaking strength by skilled observers and then also provides a good indication for possible or necessary changes of the dental prosthesis data record.

Such graphical representations can be established as individual pictures or else as video clips. They can be accessible to the person who created the dental prosthesis data record, for example by e-mail, by a web server or otherwise (by mail).

In an advantageous approach, the dental prosthesis is manufactured and subsequently photographed, so that the photos (also electronic pictures) can also be filed.

The method is advantageously integrated into a production process. In this case, it is e. g. also conceivable as regular part of a quality assurance process.

For performing the method, a correspondingly equipped computer can be provided. Moreover, a machine-readable medium or a computer program can be provided for performing the methods.

When a data record is obtained which represents the shape of a remaining tooth area, usually, a model of the remaining tooth area is made as the latter can then be separated into individual parts and can thus be optimally scanned. In the method proposed herein, however, the possibility of determining the shape of a remaining tooth area directly on the basis of the remaining tooth area is considered. Here, the shape of the remaining tooth area is, for example, determined in the oral cavity of the patient. The thus gathered data are transmitted to modeling software by which a dental prosthesis data record can be created on the basis of which a production system can manufacture the dental prosthesis.

The data record is preferably obtained with a so-called chair side system that is arranged directly at the dentist's chair. If therefore during dental treatment it becomes necessary to manufacture a dental prosthesis, the shape of the remaining tooth area can be directly obtained. This is advantageously performed with an optical probe which can, for example, well measure cavities in teeth.

While the data record is advantageously obtained at the dentist himself, the modeling software can, for example, be employed in a dentistry laboratory or a production center. This relieves the dentist of such work. The production system and the modeling software neither have to be at the same location as the production system can be, for example, in a central production center, whereas the modeling software is used by a dental laboratory technician or in a dentistry laboratory.

The manufacture of a dental prosthesis in a production center normally has great advantages with respect to the quality of the dental prostheses as here corresponding apparatuses and experience are available.

The dental prosthesis is advantageously an inlay, but it can also be an overlay, a crown, a part of an implant or a bridge.

In the method, the dental prosthesis data record is advantageously at the same time examined with finite element methods. This can be made at the location where the dental prosthesis data record is created as then the dental prosthesis data record can be adjusted on the basis of this examination. However, the examination can also take place at the location of the manufacture of the dental prosthesis as here condense calculation capacity is available by which one can quickly check whether it makes sense to produce such a dental prosthesis at all.

For performing the method, a correspondingly assembled system can be provided.

Some dentistry laboratories have digitally controllable milling machines by means of which smaller dental prostheses can be manufactured relatively quickly.

In production centers, normally higher-quality milling machines are available by means of which one can also easily manufacture large dental prostheses. For doing so, systems for calculating milling data are available in the production centers, which calculate milling data required for the control of the milling machine from data representing a dental prosthesis. These calculations require considerable calculating capacities. In the method, the execution of the milling data calculation can be performed at one location, the milling data can then be transmitted to another location by remote data transmission, and at the other location, the dental prosthesis can be manufactured. This makes it possible to have the milling data calculation performed in a production center, but to carry out the dental prosthesis manufacture with a milling machine in the dentistry laboratory. This also has the advantage that the dental prosthesis is available directly in the dentistry laboratory. With a manufacture of the dental prosthesis in the production center, the dental prosthesis first has to be dispatched.

Instead of manufacturing dental prostheses with milling machines, construction methods can also be employed, such as laser lithography, where liquid or powdery medium is applied layer upon layer and the respective uppermost layer is hardened by laser irradiation. Thus, very diverse structures can be manufactured. Representatively of general manufacturing methods for dental prostheses, here the milling method will be discussed. However, in all manufacturing methods, the same problems arise, as in each case a data record describing a dental prosthesis has to be converted into manufacturing data that control a machine which can naturally by very elaborate.

It is furthermore advantageous if the dental prosthesis data record is also created at the first location, i. e. for example in the dentistry laboratory. The dental prosthesis data record can then also be transmitted to the production center by remote data transmission.

This relieves the dental laboratory technician of the maintenance and purchase of systems for calculating milling data, and he can make use of them quasi as a service of a production center, or in this case rather a calculation center.

However, it is also possible that in the dentistry laboratory only the data record that describes the remaining tooth area is gathered, that this data record is sent to the production center and that there the data record that represents the dental prosthesis is created.

The transmission of the milling data from the second location or the first location can, for example, be performed only after a decision on whether the transmission is to take place at all. Of course, it is also possible that the milling data are not transmitted but rather forwarded to a milling machine available at a second location, i. e. for example within the production center. For performing the method, a correspondingly equipped system can exist.

In other methods, it can be examined whether the milling data are to be transmitted to the first location or whether they are to be forwarded to a milling machine at the second location. For doing so, the data record representing the dental prosthesis or only a part thereof as well as the record of the milling data can be examined.

The manufacture of large dental prostheses can thus be performed in the production center whereas the manufacture of small dental prostheses can be performed in the dentistry laboratory with their smaller milling machines. For doing so, a correspondingly equipped system can also exist.

Even independently of where or how a dental prosthesis data record was created, one can generally examine whether the milling data are transmitted to a remote location or to a near location by means of a dental prosthesis data record or a milling data record. For doing so, a corresponding computer, a machine-readable medium or a computer program with program code means for performing the method can be provided.

In all methods, one can perform the examination of the dental prosthesis data record with finite element methods at one or several of the different locations.

BRIEF DESCRIPTION OF THE DRAWINGS

Advantageous embodiments of the invention are to be illustrated with reference to the accompanying Figures, wherein.

DETAILED DESCRIPTION OF THE INVENTION

Figure 1A:
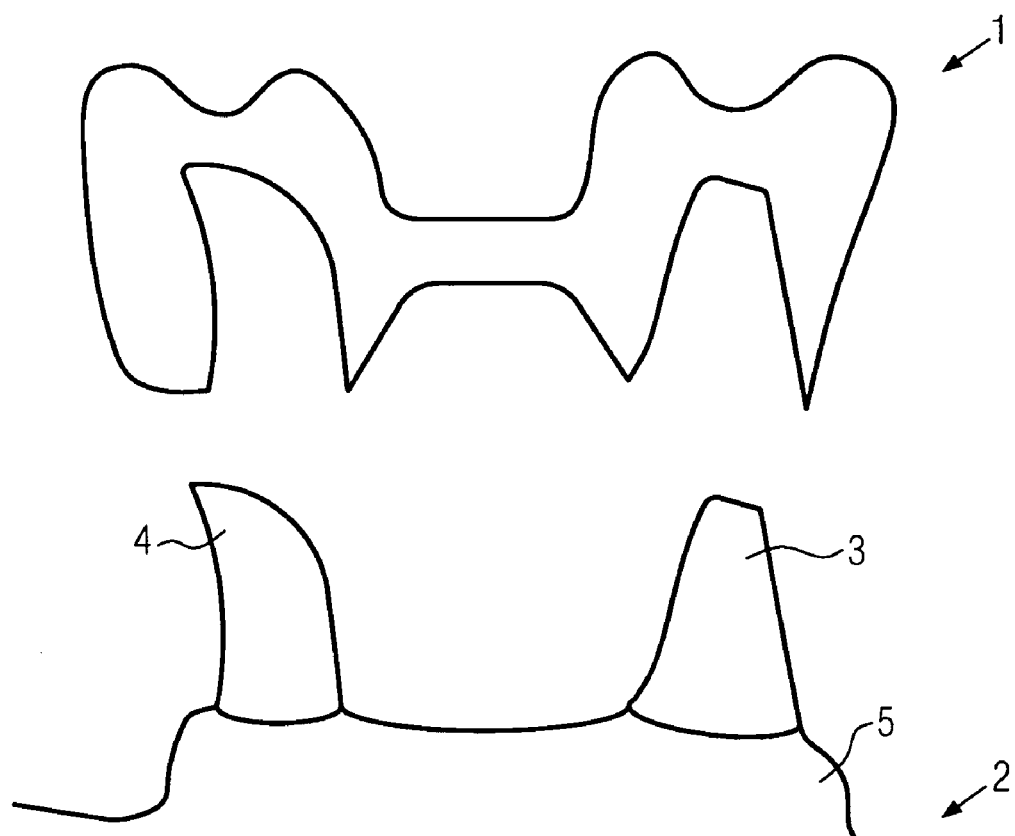
FIGS. 1a and 1b show a dental prosthesis and a remaining tooth area in different positions relative to one another.

FIG. 1a shows a dental prosthesis 1 located above a remaining tooth area 2. The remaining tooth area 2 comprises two prepared stumps of the tooth 3 and 4 as well as a gingival area 5.

Figure 1B:
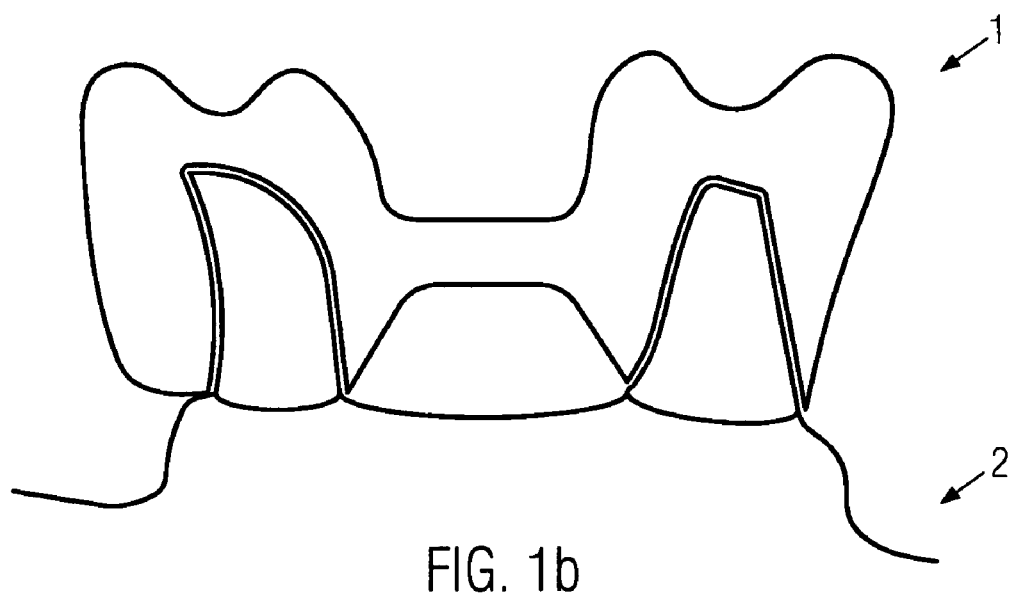

In FIG. 1b, the dental prosthesis 1 is shown as it is fitted on the remaining tooth area 2. Here, the dental prosthesis 1 is a bridge. For the remaining tooth area 2 as well as for the dental prosthesis 1, there can be a digital data record representing the remaining tooth area or the dental prosthesis 1. Such a data record representing a dental prosthesis 1 can be examined with a finite element method.

Figure 2:
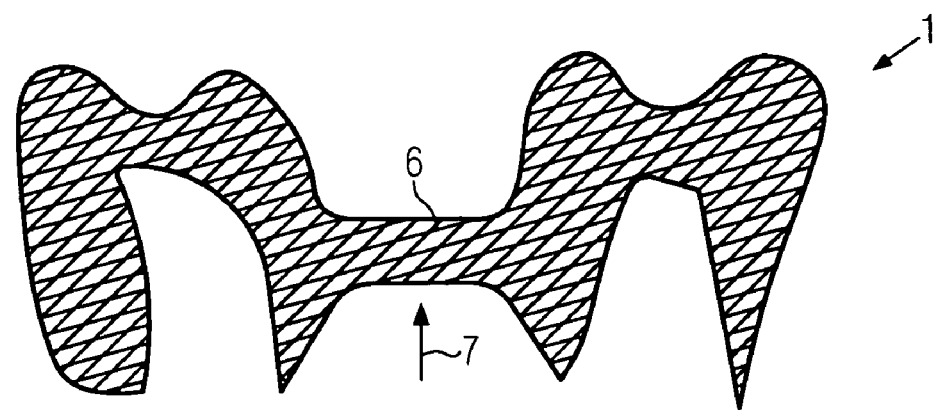
FIG. 2 shows a dental prosthesis with finite elements.

In FIG. 2, it is schematically shown how the data record of the dental prosthesis 1 was subdivided into a large number of small elements 6 (finite elements) by means of appropriate software. This approach permits to simulate tensions that can occur in the dental prostheses due to exterior forces. For example, one can examine what force is required for breaking the dental prosthesis at the site marked by arrow 7. The schematic subdivision into finite elements 6 shown in FIG. 2 is only given by way of example. It will be advantageous to consider finite elements varying in size and shape.

Figure 3:
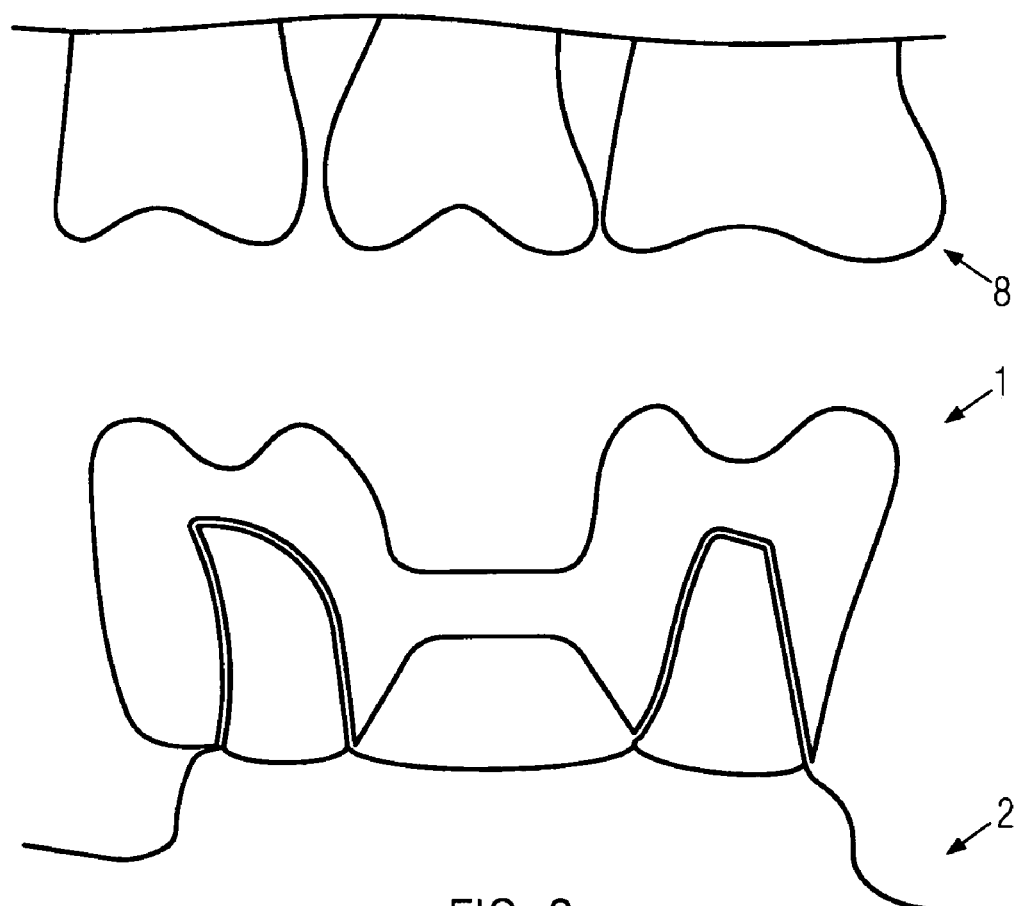
FIG. 3 shows a dental prosthesis between upper jaw and lower jaw.

FIG. 3 shows how the dental prosthesis 1 is fitted on a remaining tooth area 2. Above the dental prosthesis 1, furthermore a tooth area 8 is represented which corresponds to the opposite jaw. Data representing the remaining tooth area 2 as well as the remaining tooth area 8 can be considered in the examination of the data record of the dental prosthesis 1.

A dental prosthesis 1 is, for example, milled out of a blank during manufacture. In the process, forces that can also lead to a break are applied on the dental prosthesis being formed. As a rule, the dental prosthesis is not milled out of the end material, but in case of ceramics out of a preliminary stage which is subsequently fired whereby it obtains its complete hardness. The material which is worked by milling, however, is comparably brittle. In order to avoid a break in the process, the data record of the dental prosthesis can therefore also be examined for stability during production.

Figure 4A:
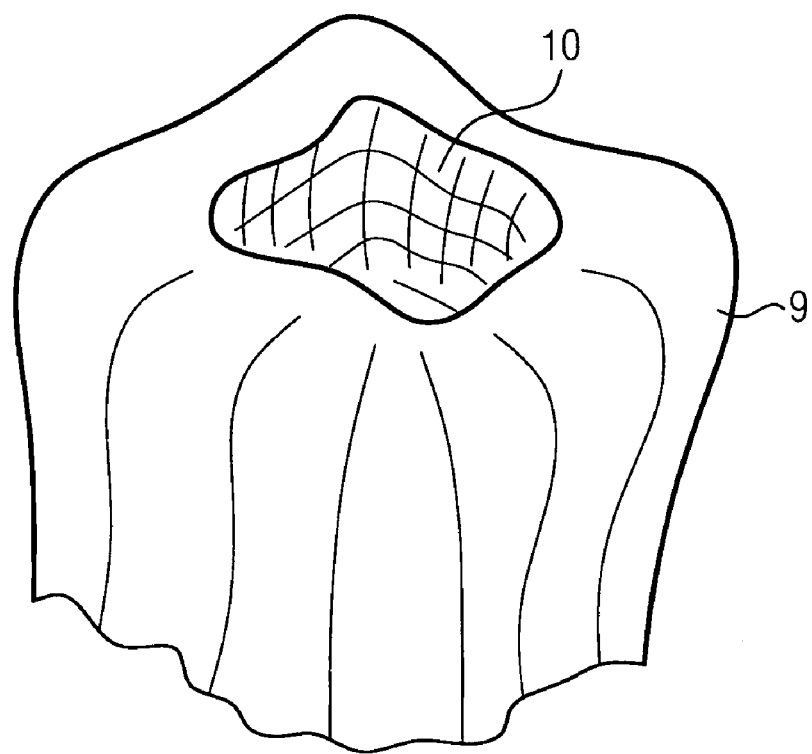
FIGS. 4a and 4b show a tooth with a cavity.

In FIG. 4a, a tooth 9 into which a cavity was milled is schematically shown. The cavity 10 can, for example, have been made for removing caries. An inlay can be provided for filling the cavity 10.

In order to determine the shape of the inlay, the shape of the cavity 10 has to be determined. This can, on the one hand, be performed by producing a mould of the cavity 10 and the tooth 9 by means of which then a model of the hollowed tooth 9 is created.

However, it is easier to determine the shape of the cavity 10 directly. This can be performed, for example, with an optical probe 11 (see FIG. 5) which is brought into a corresponding position relative to the cavity 10, so that the same can be completely scanned.

Instead of gathering a data record from only one tooth 9 and one cavity 10, one can also scan a larger remaining tooth area. This can be performed, for example, by individual scans from predetermined directions.

Figure 5:
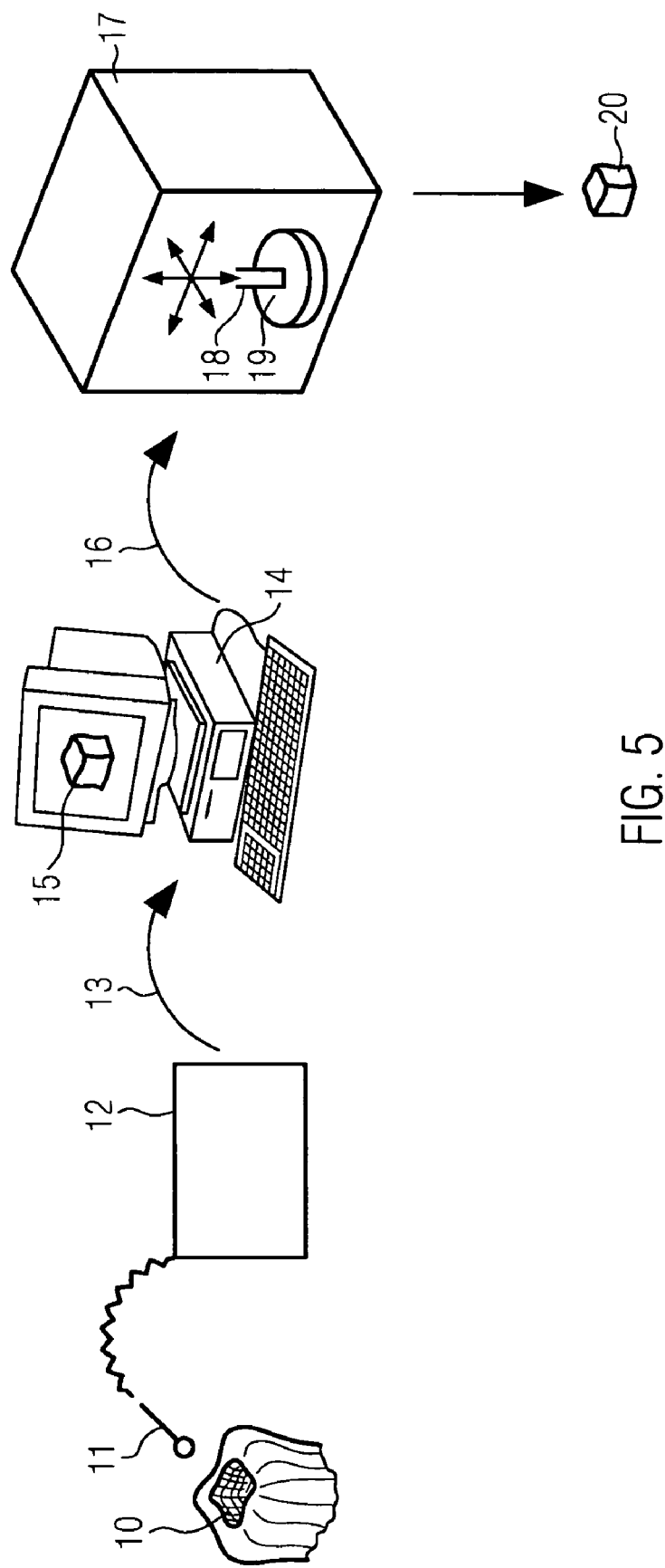
FIG. 5 shows a schematic representation of a procedure for the manufacture of a dental prosthesis.

The thus obtained data can be stored or processed in a unit 12 (see FIG. 5). From there, the data representing the remaining tooth area can be transmitted to modeling software 14. The software can also be installed, for example, in a computer with the aid of which a dental prosthesis data record 15 is created. The modeling software can create the dental prosthesis data record all-automatically, i.e. without any human help, or semiautomatically on the basis of operator inputs.

The thus obtained dental prosthesis data record 15 is transmitted to a production system 17 which, for example, first calculates milling data and subsequently controls a cutter head 18. With the cutter head 18, one can mill a dental prosthesis 20 out of a blank 19. Instead of milling, one can also employ any other method of manufacturing dental prostheses, such as laser lithography. The dental prosthesis- can be dispatched to the patient's location, so that the dental prosthesis 20 can be fitted.

The data record representing the shape of the remaining tooth area is preferably obtained at the dentist. The modeling of the dental prosthesis data record is advantageously made by a dental laboratory technician or in a dentistry laboratory, respectively. The manufacture of the dental prosthesis or the production system 17, respectively, is preferably located in a production center. In this manner, the various components which are employed in the manufacture of dental prostheses can be optimally linked so that an optimal utilization can be obtained. The production centers having high throughput capacities can optimally utilize the appliances and correspondingly optimize them, while in various dentistry laboratories, the systems for the creation (modeling) of dental prosthesis data records can be optimally employed and correspondingly optimized. Here, furthermore a procedure wherein the production is not executed in the production center itself, but where the manufacturing data record is rather calculated like in a computer center and sent to the dentistry laboratory is particularly advantageous (also see below). There, the dental prosthesis can be manufactured, so that it is directly at the dental laboratory technician's hand. In the computer center, the quality assurance and filing can then be possibly centrally performed for documentation purposes.

The transmission 13, 16 is performed, for example, via Internet which permits the transmission of relatively large data volumes. Other remote data transmission means are also possible. However, it is also possible that two of the components 12, 14, 17, or else all three of them are with the dentist.

Figure 4B:
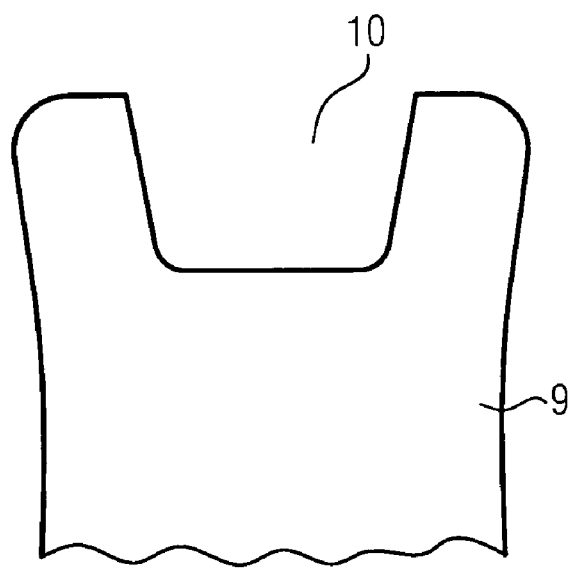

While in FIGS. 4 and 5 the case of an inlay is shown, an overlay, a crown, a part of an implant or a bridge can also be manufactured in this manner.

Figure 6:
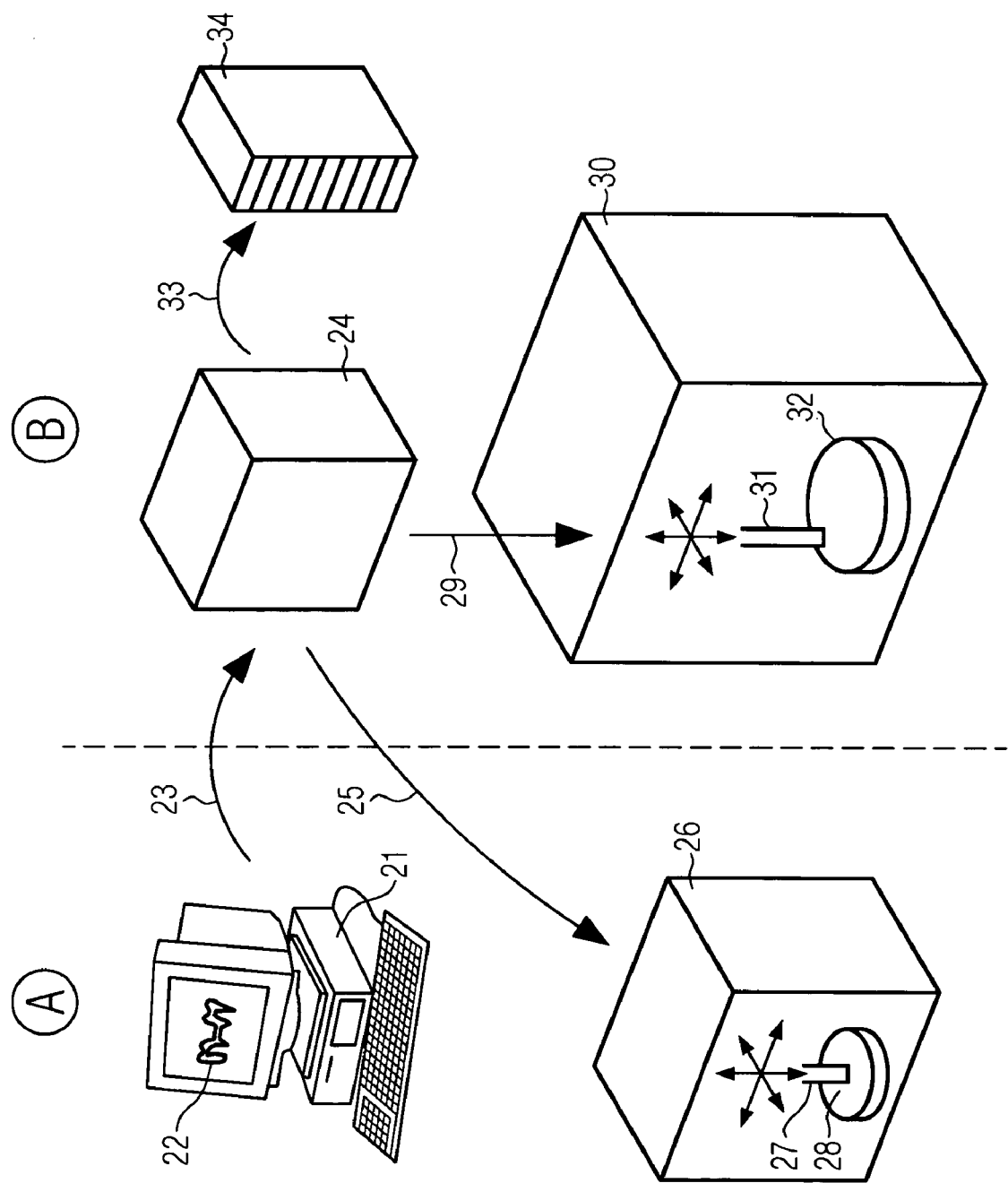
FIG. 6 shows another schematic representation of a method for the manufacture of a dental prosthesis.
Figure 7:
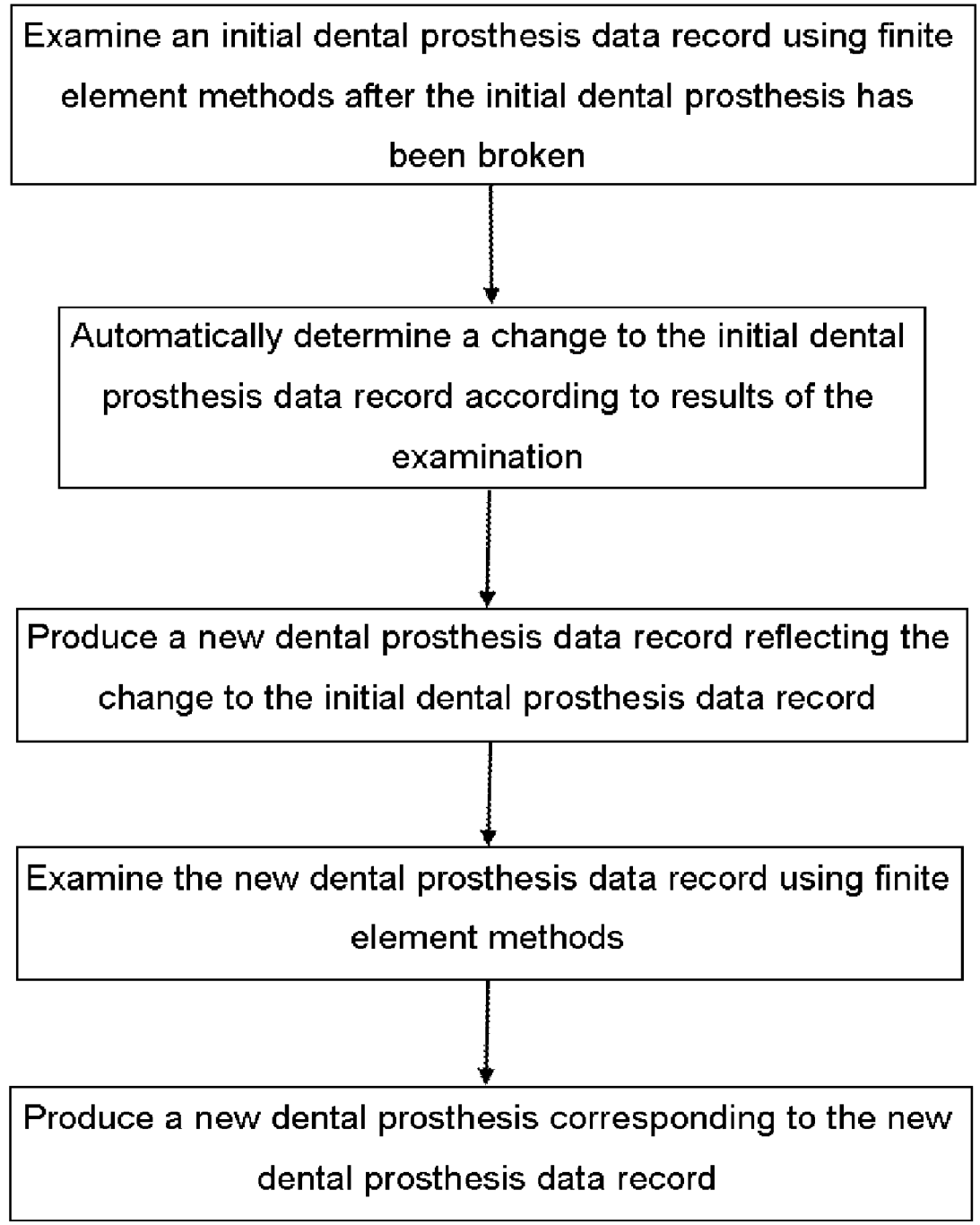
FIGS. 7-25 are flow diagrams illustrating different aspects of the method of the invention.
Figure 8:
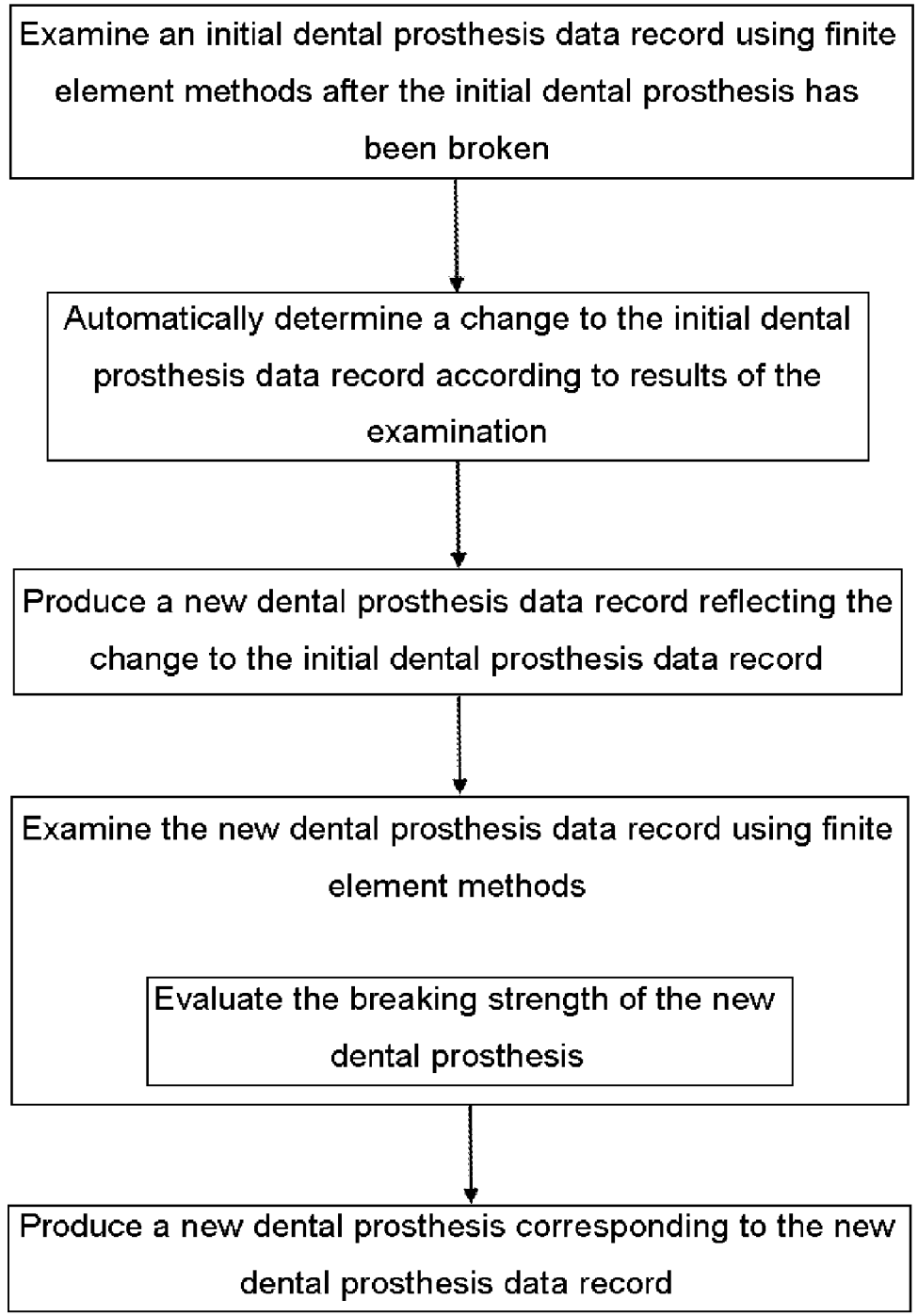
Figure 9:
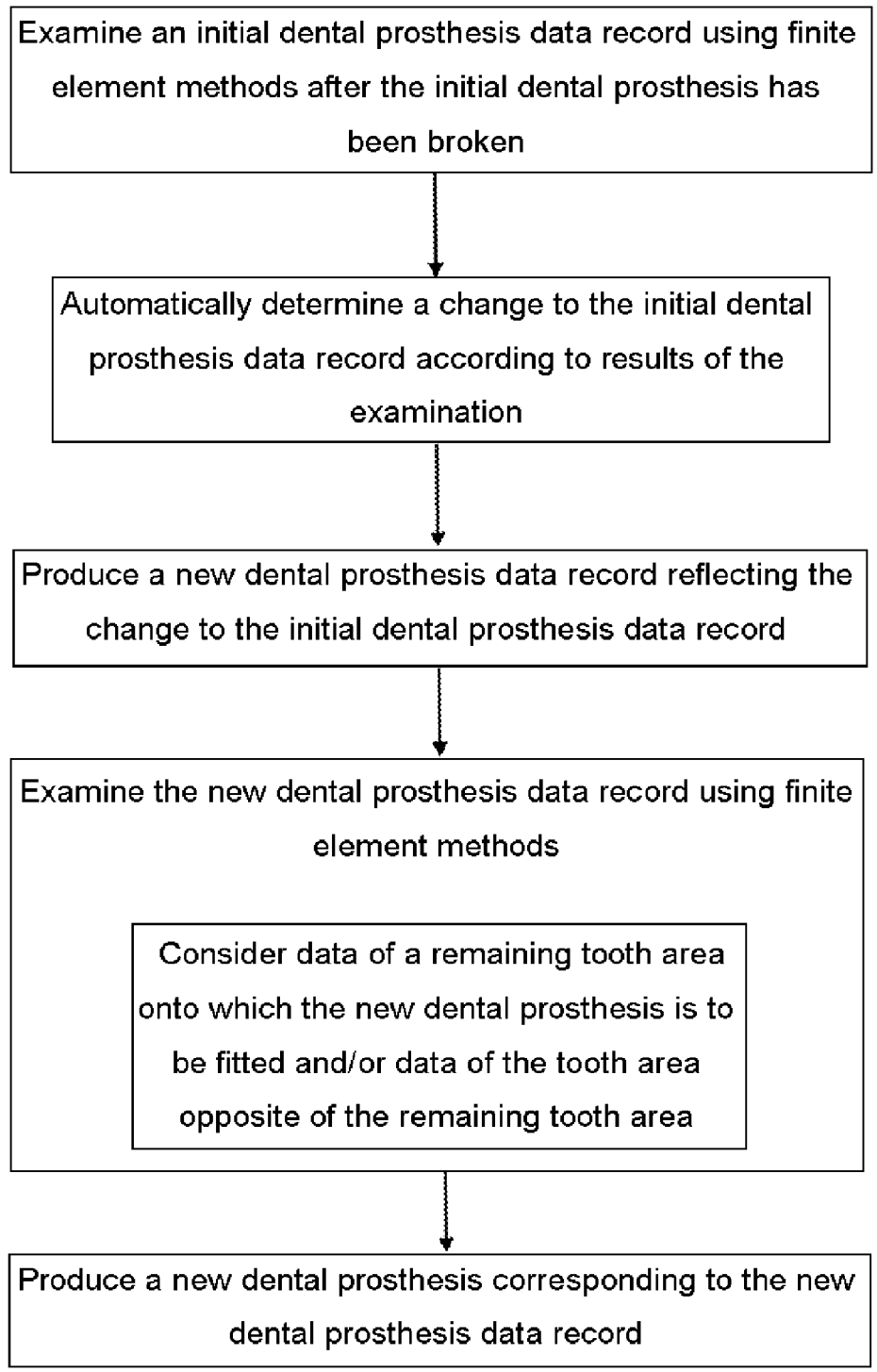
Figure 10:
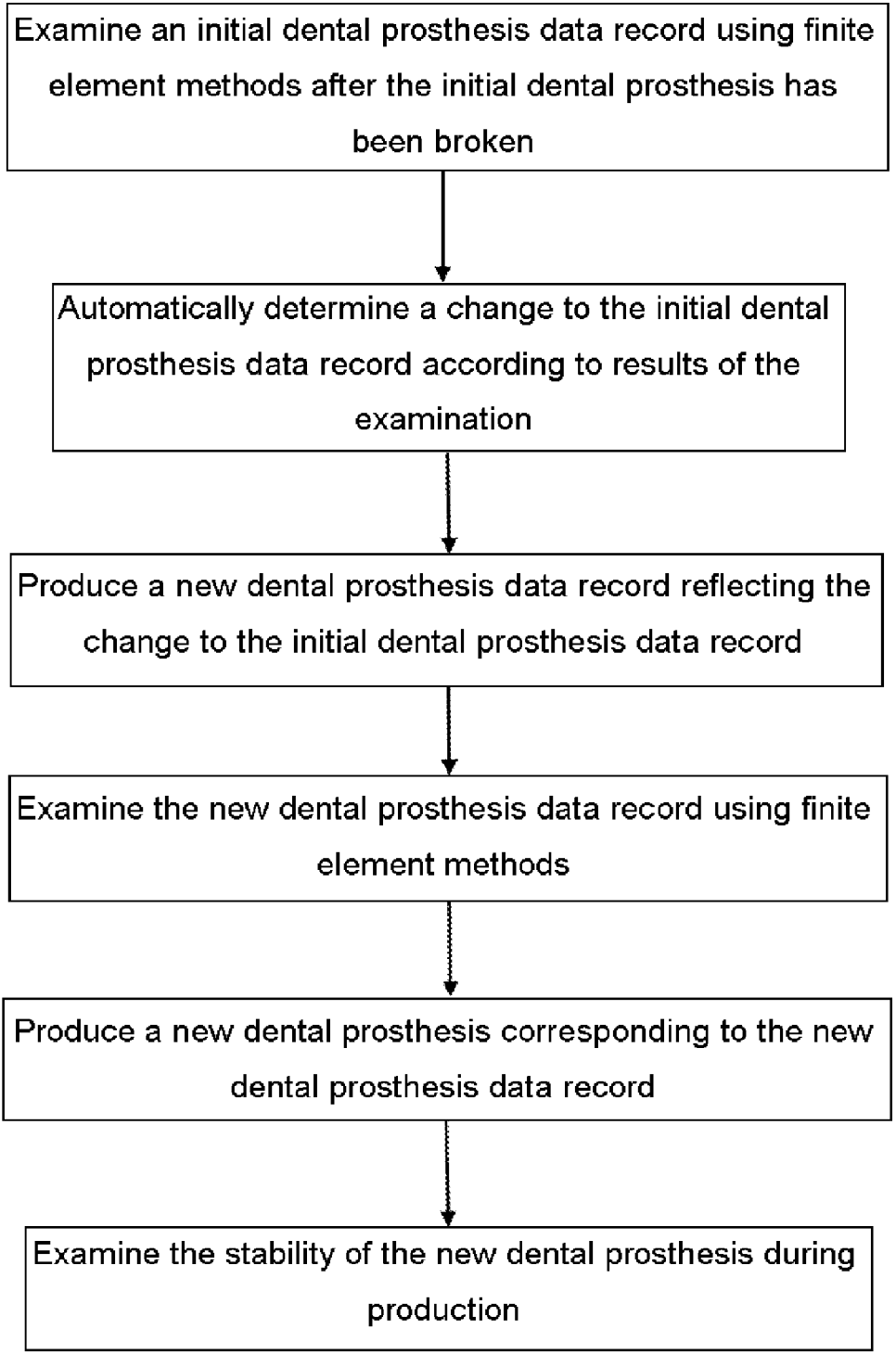
Figure 11:
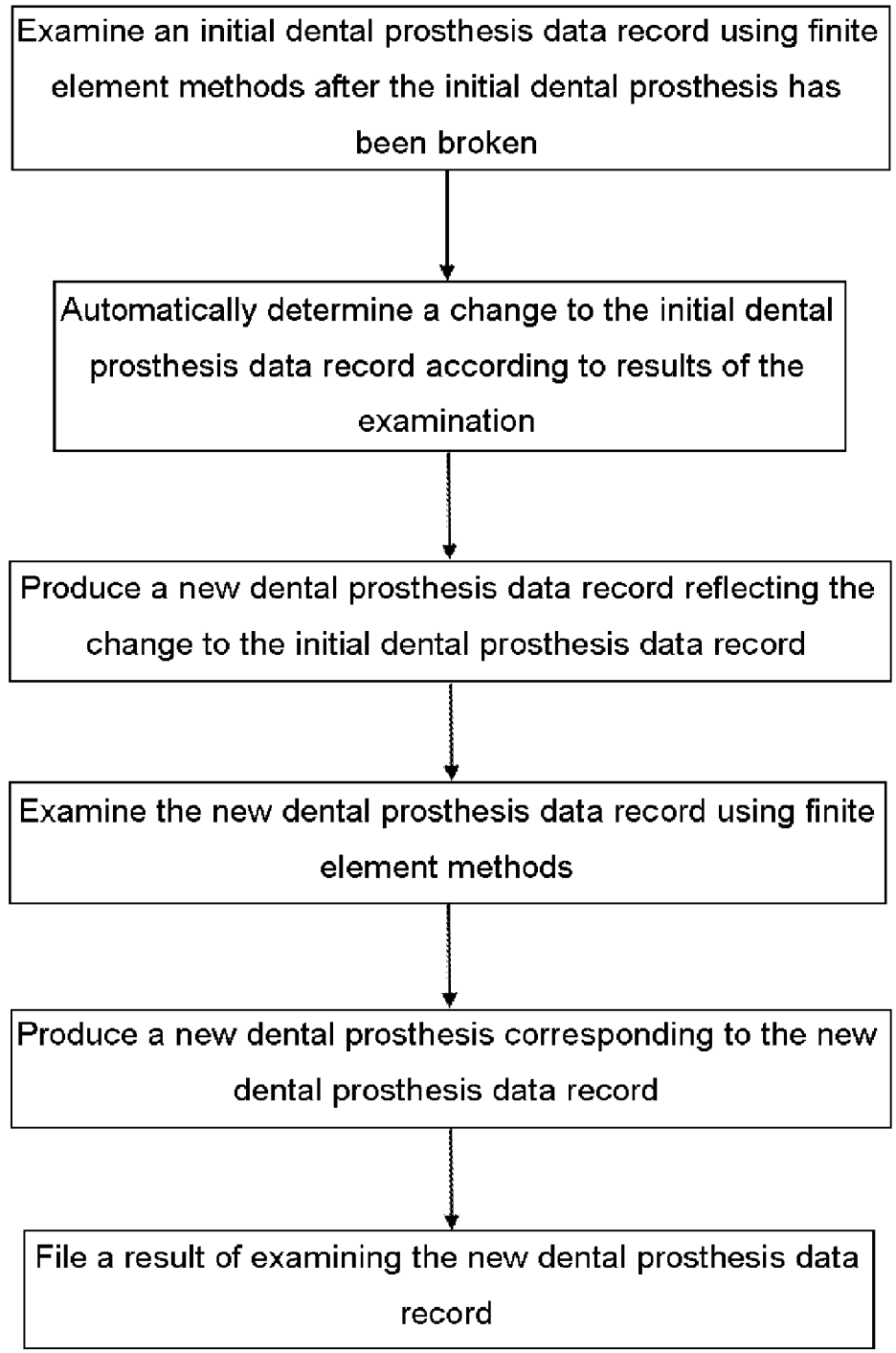
Figure 12:
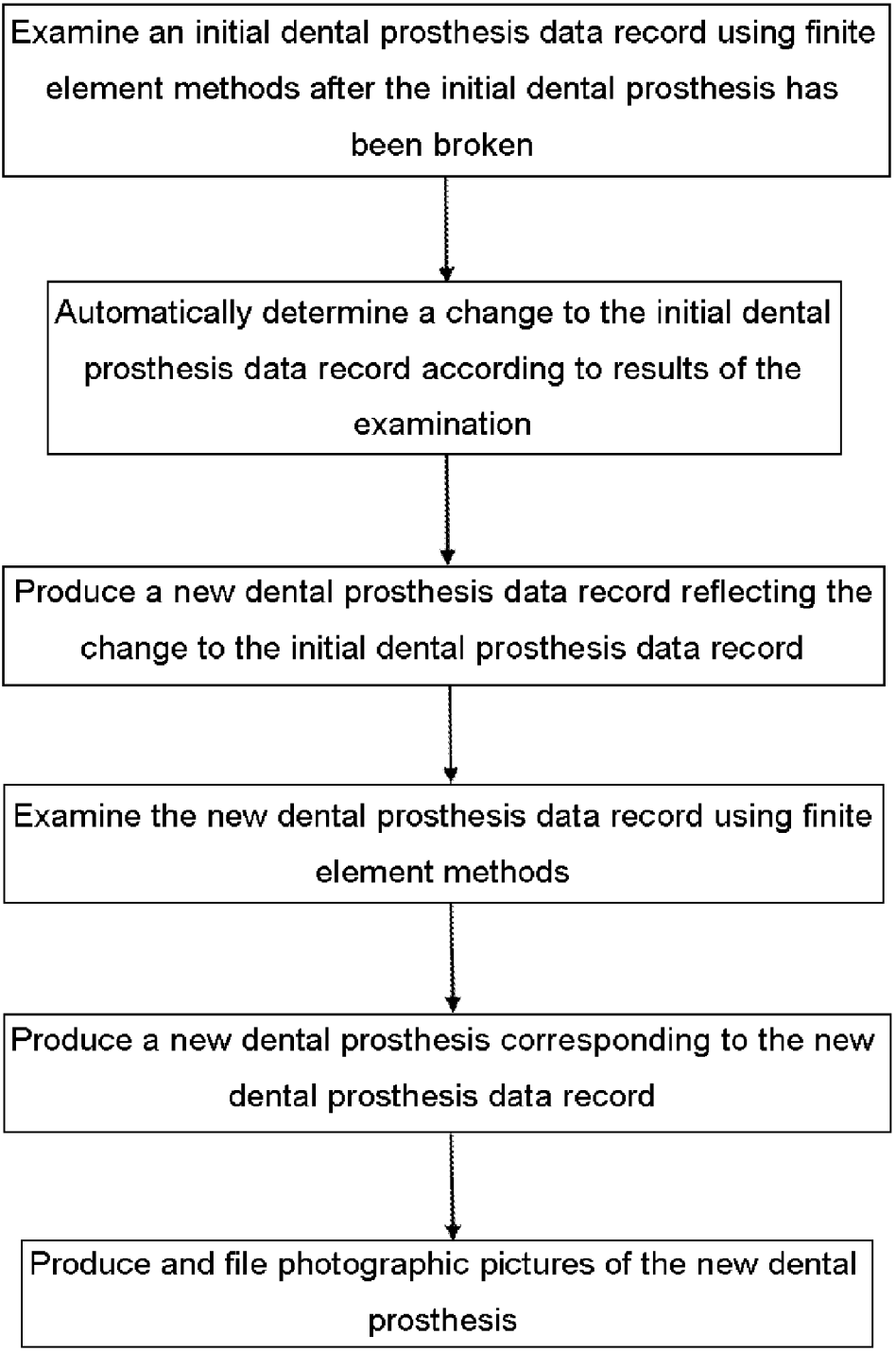
Figure 13:
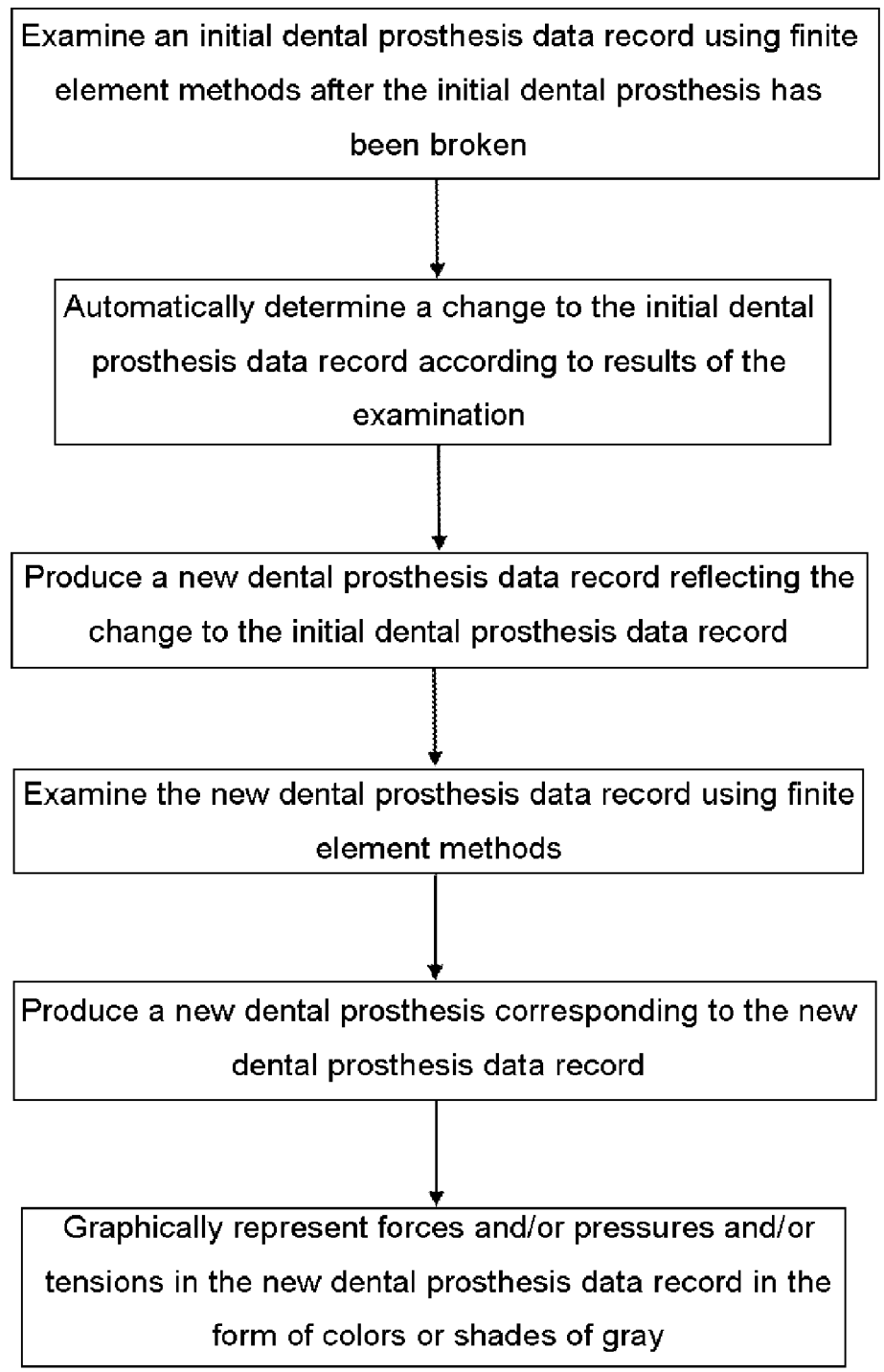
Figure 14:
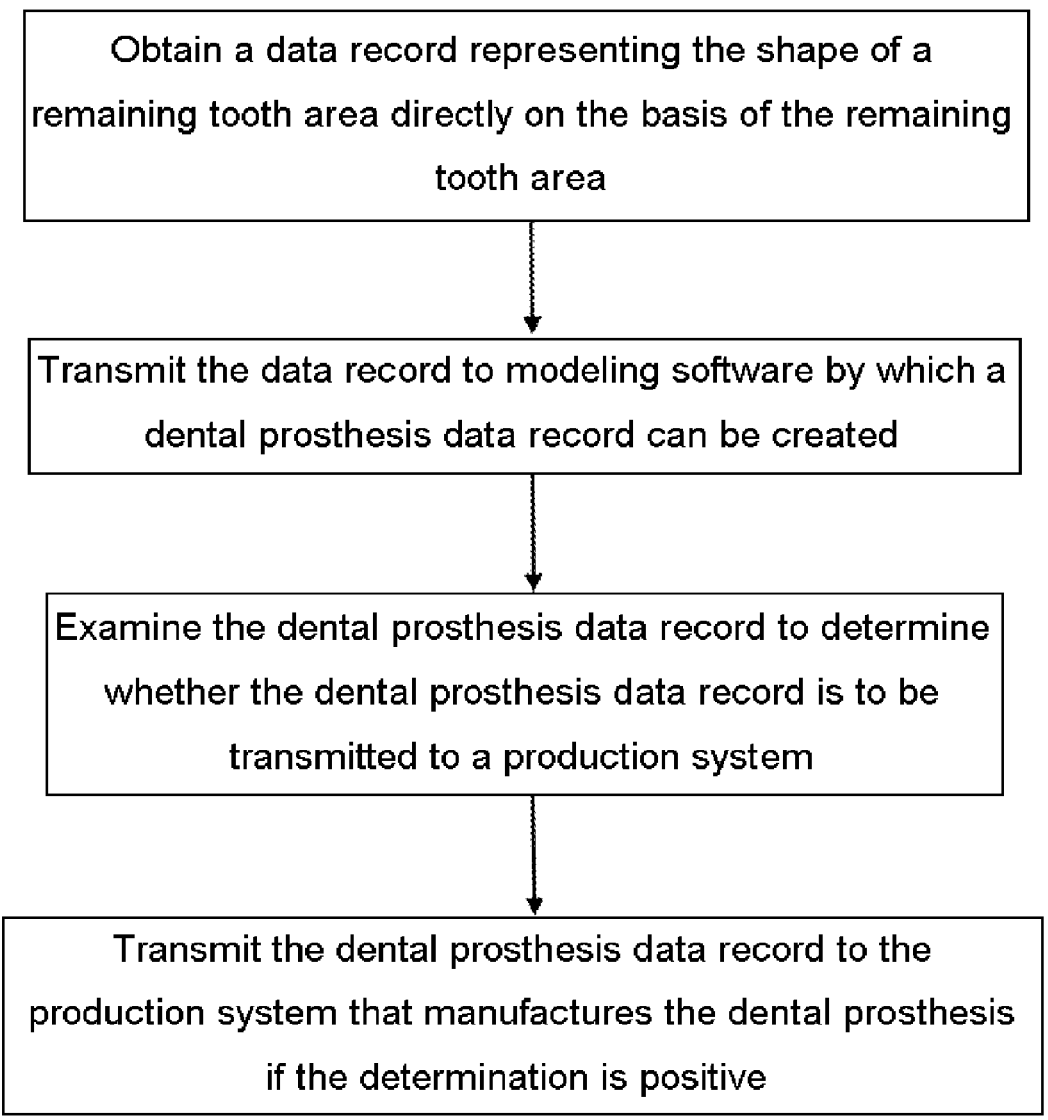
Figure 15:
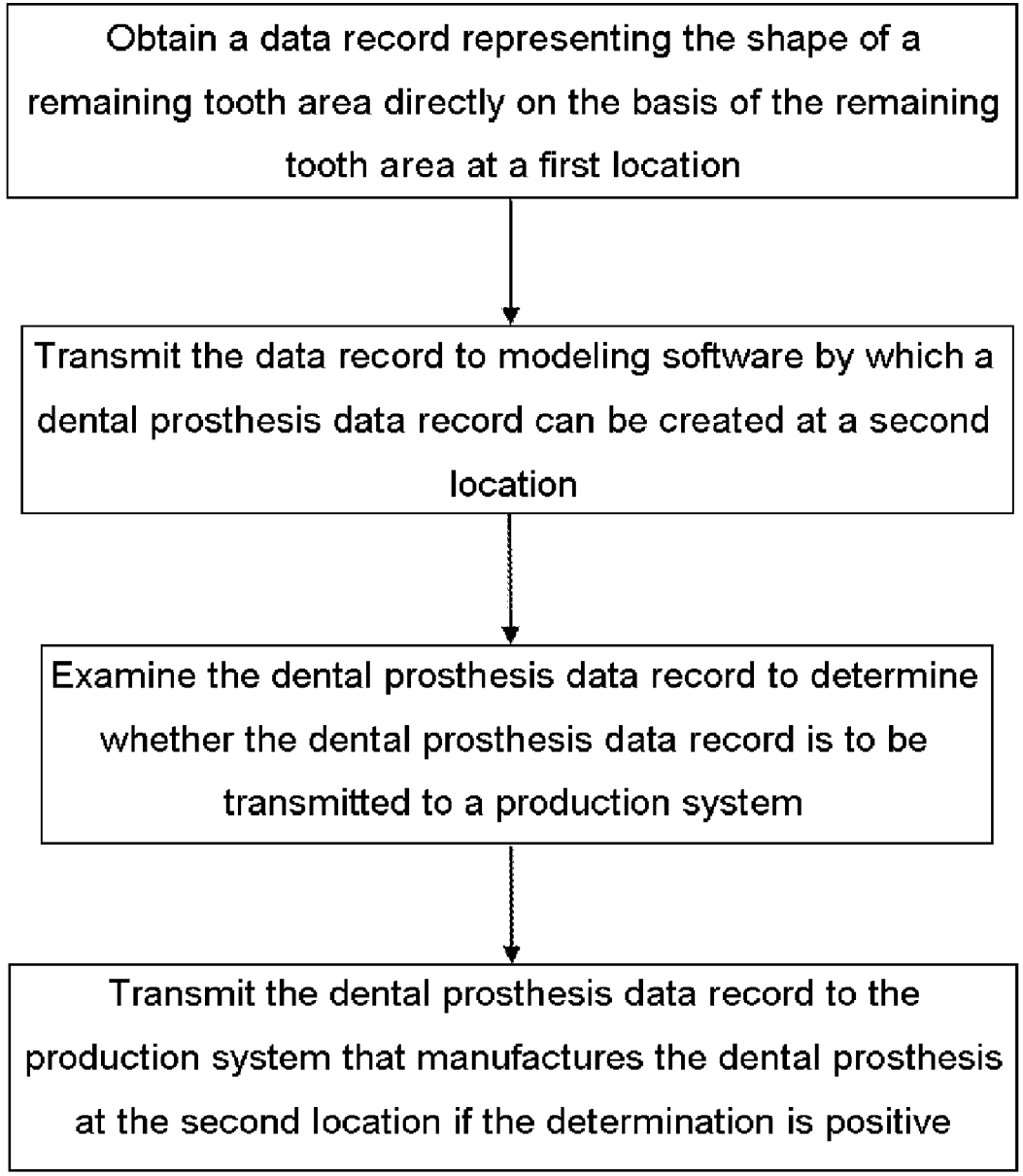
Figure 16:
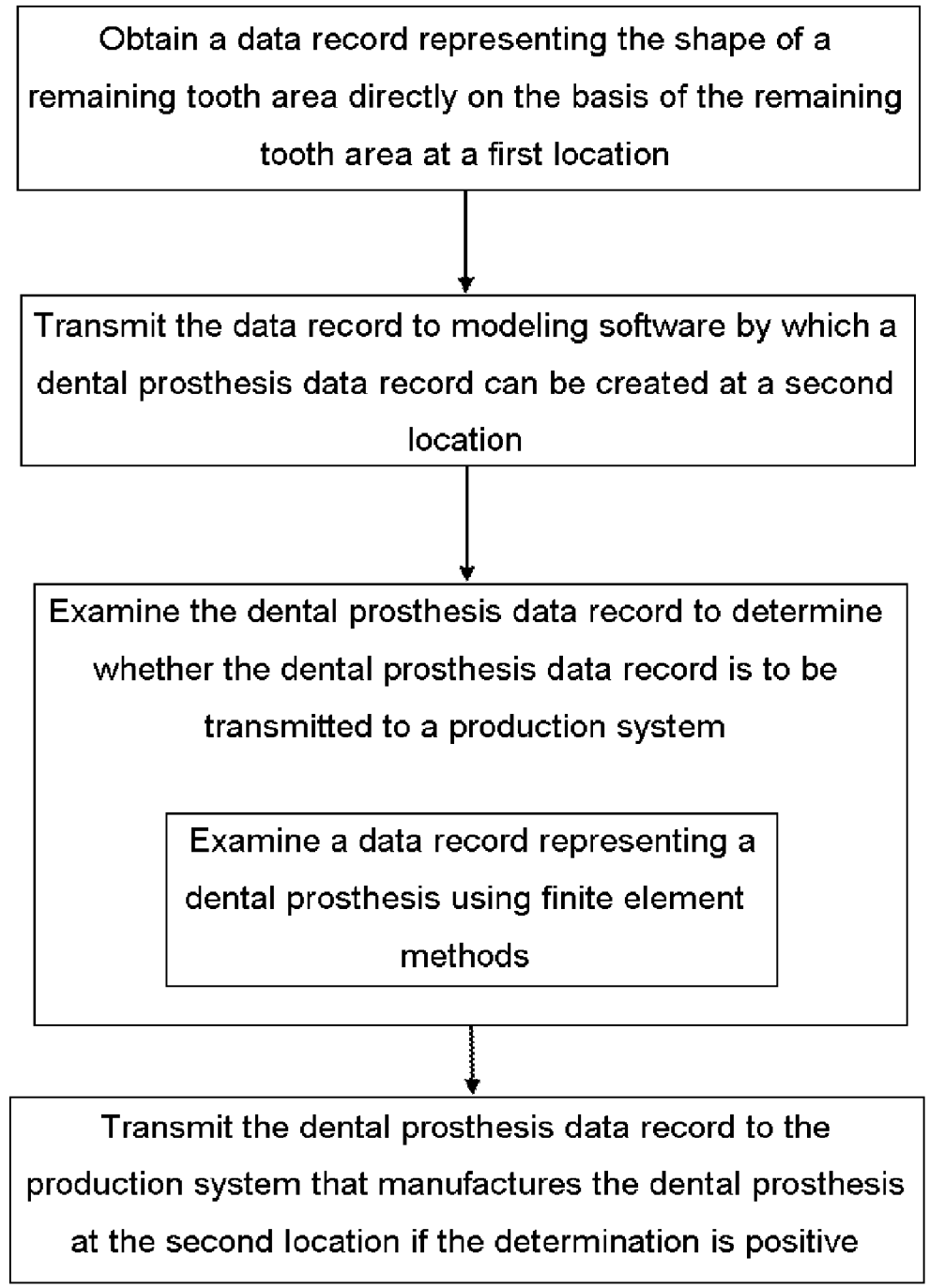
Figure 17:
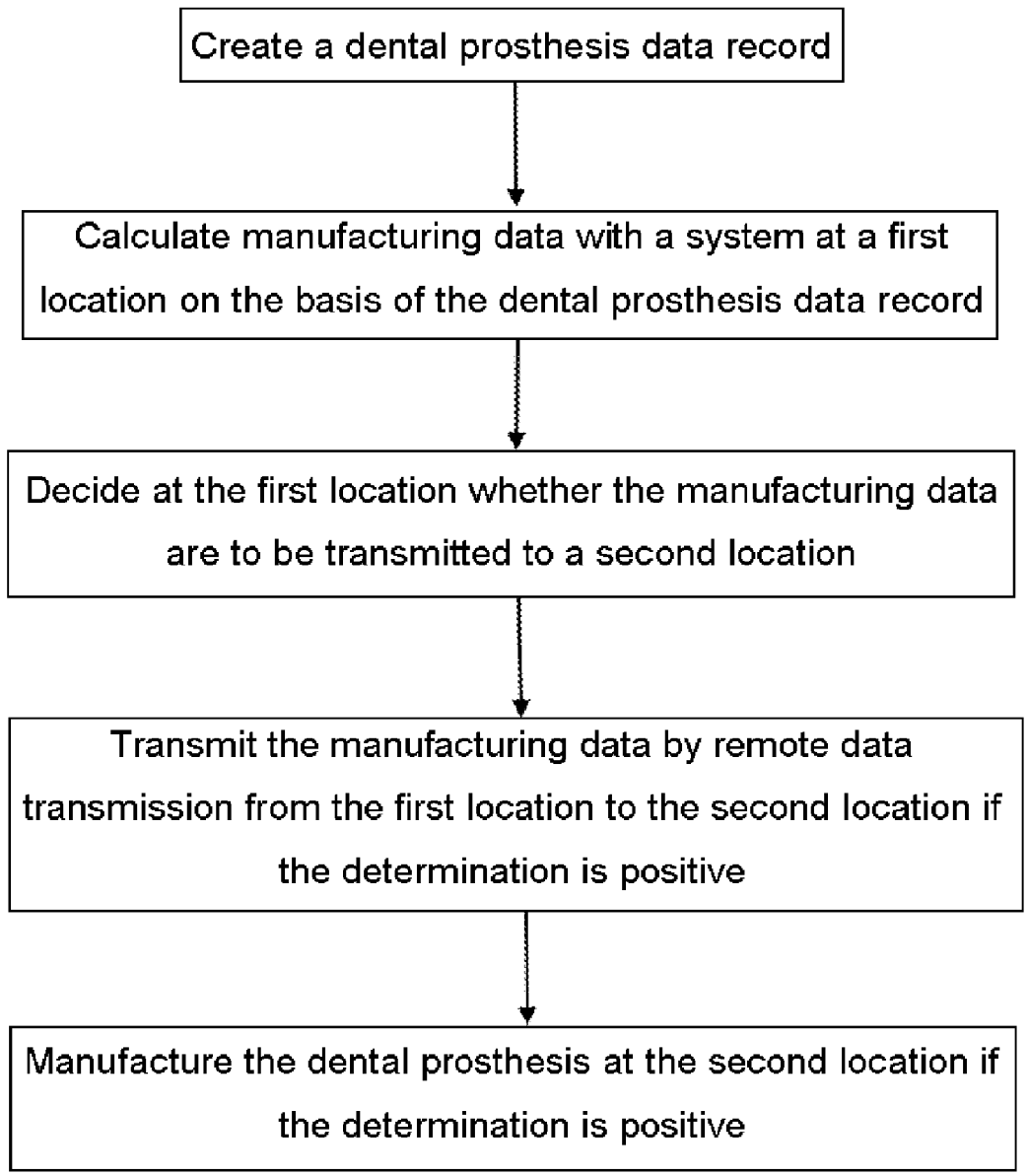
Figure 18:
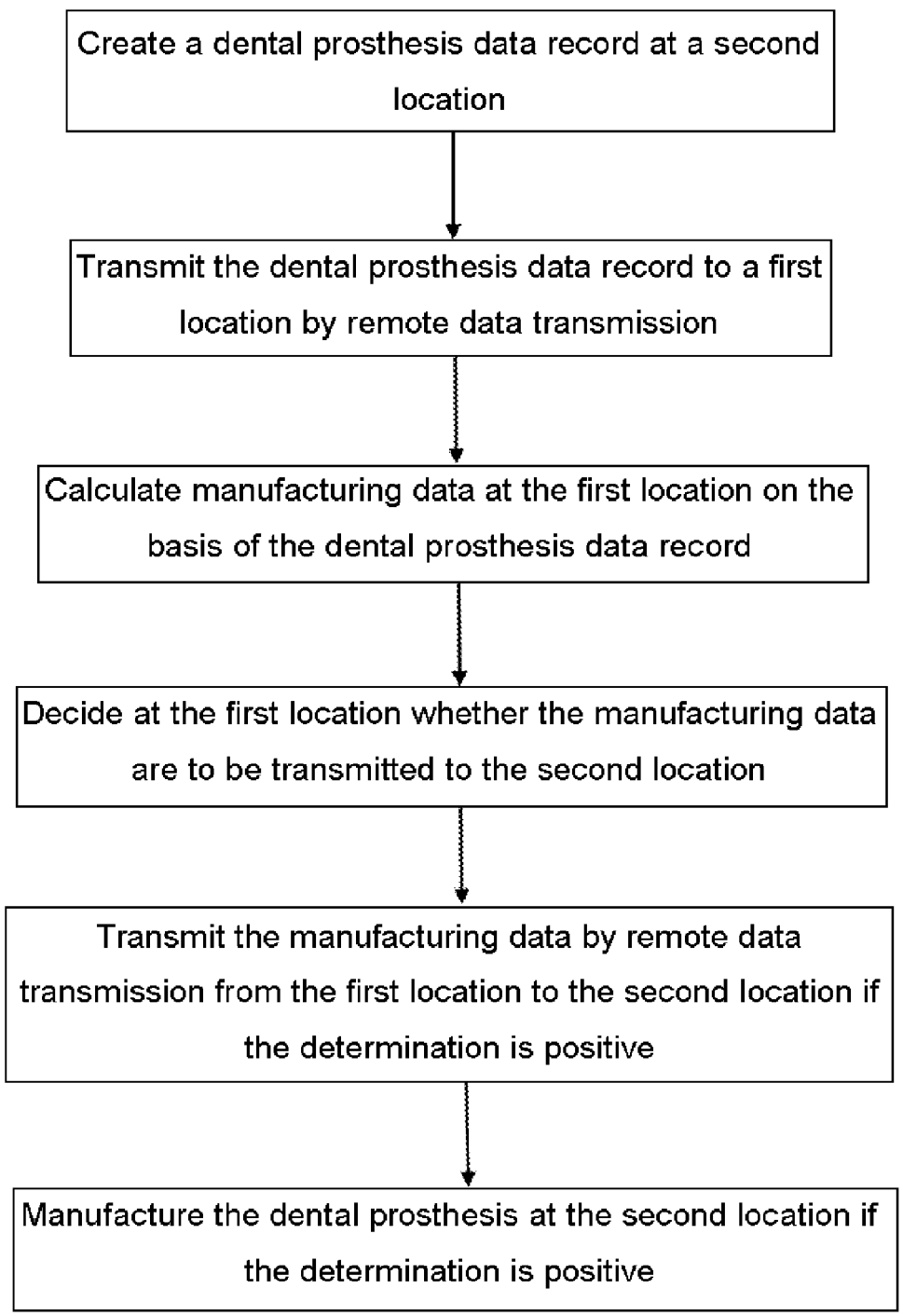
Figure 19:
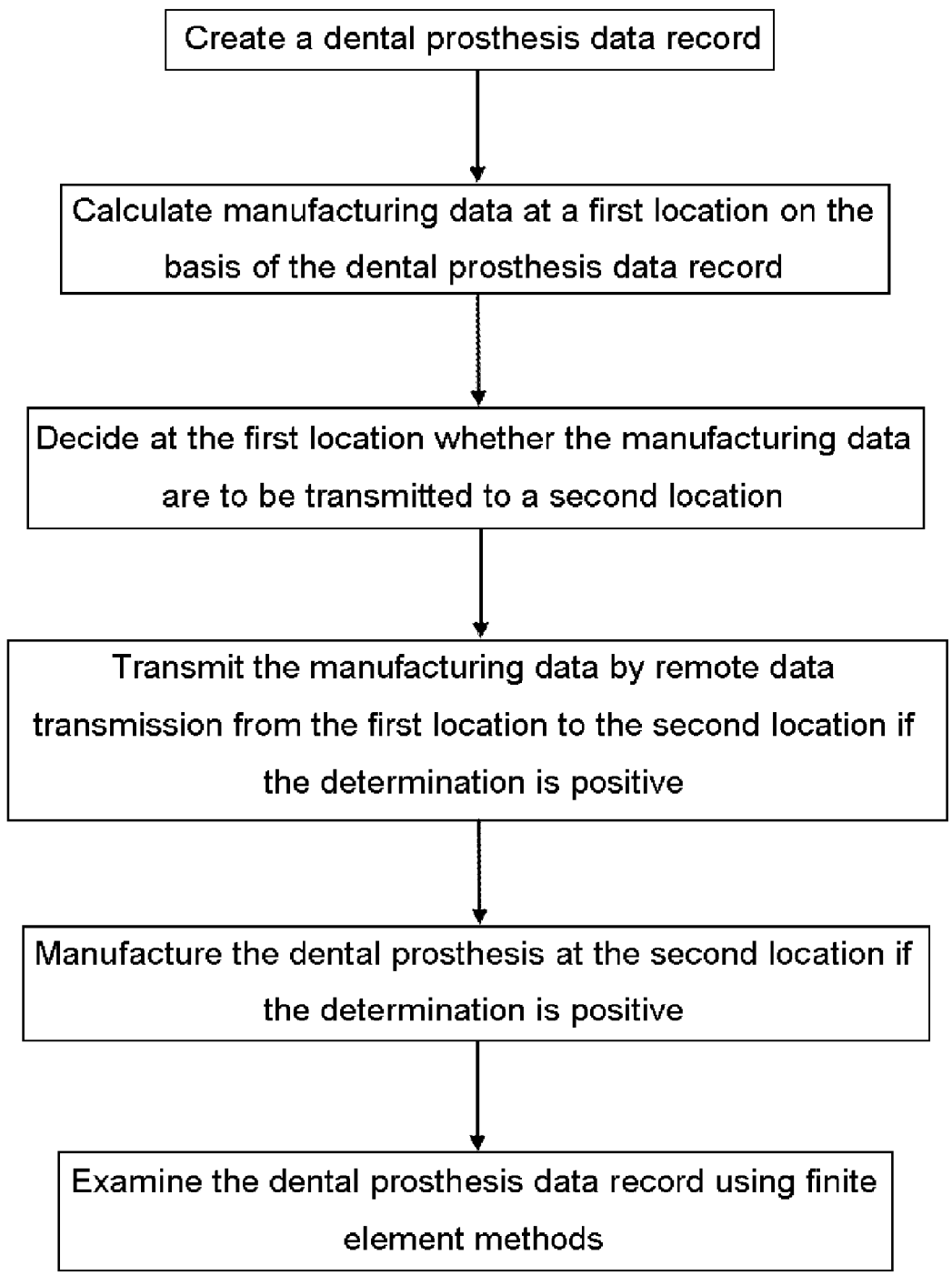
Figure 20:
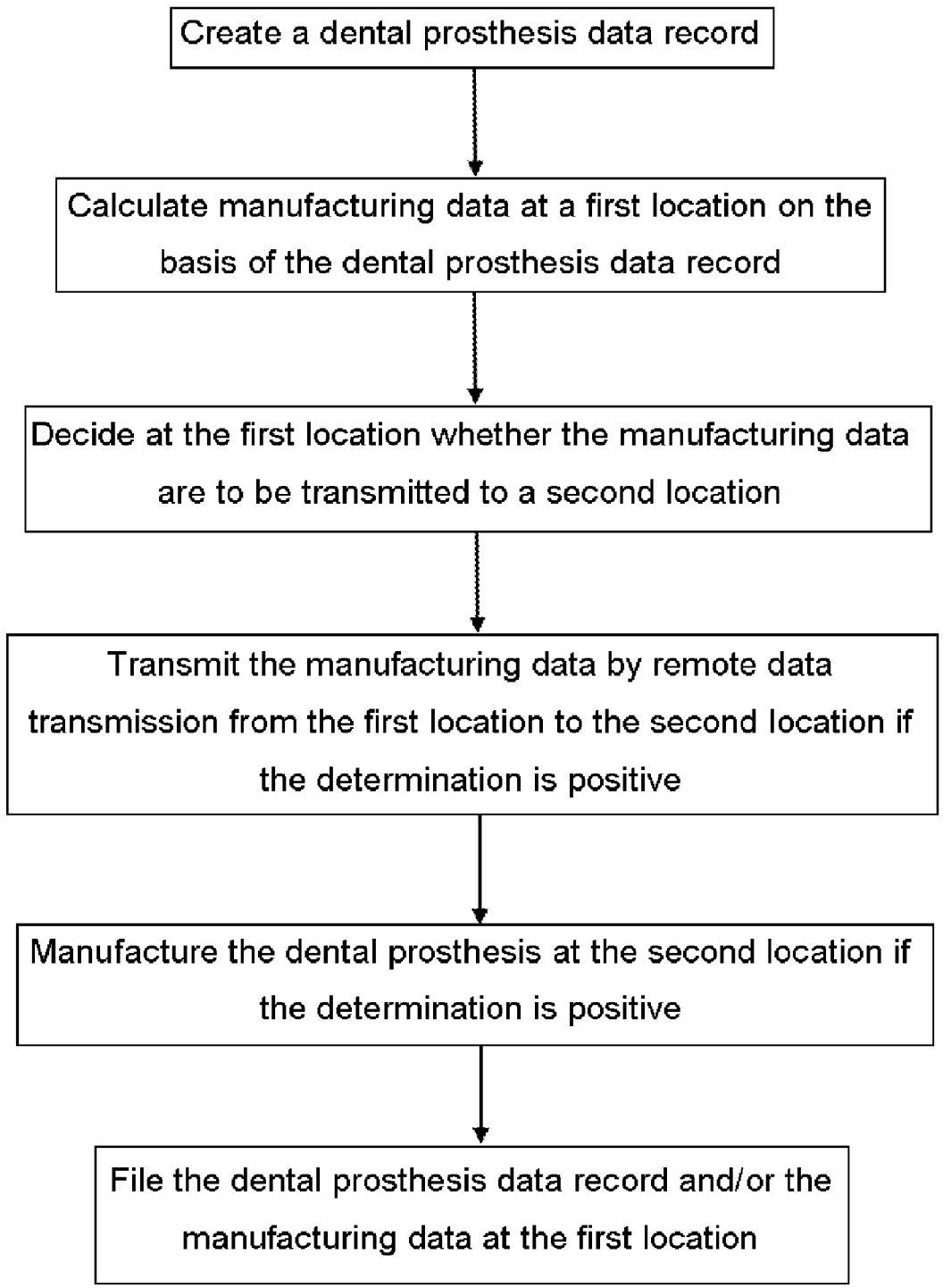
Figure 21:
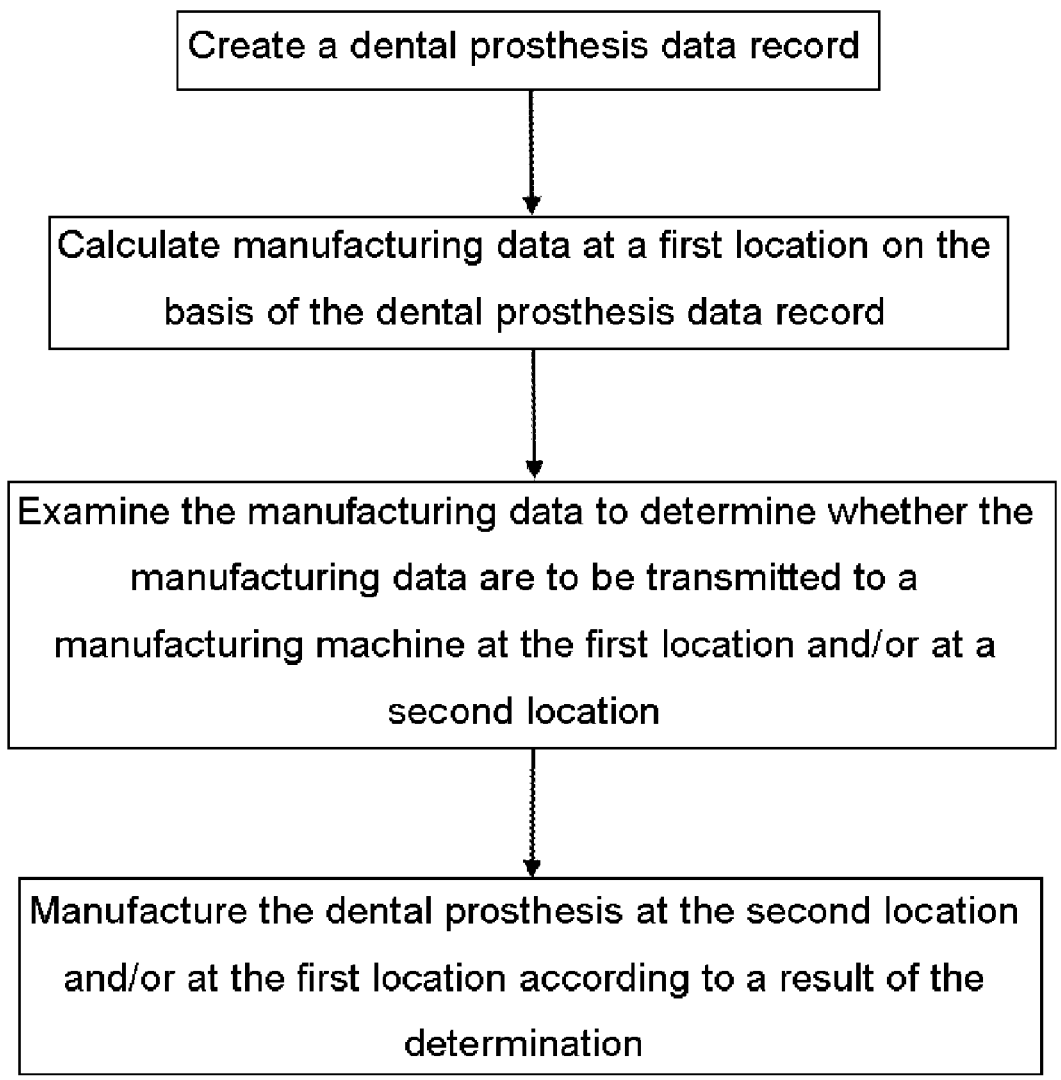
Figure 22:
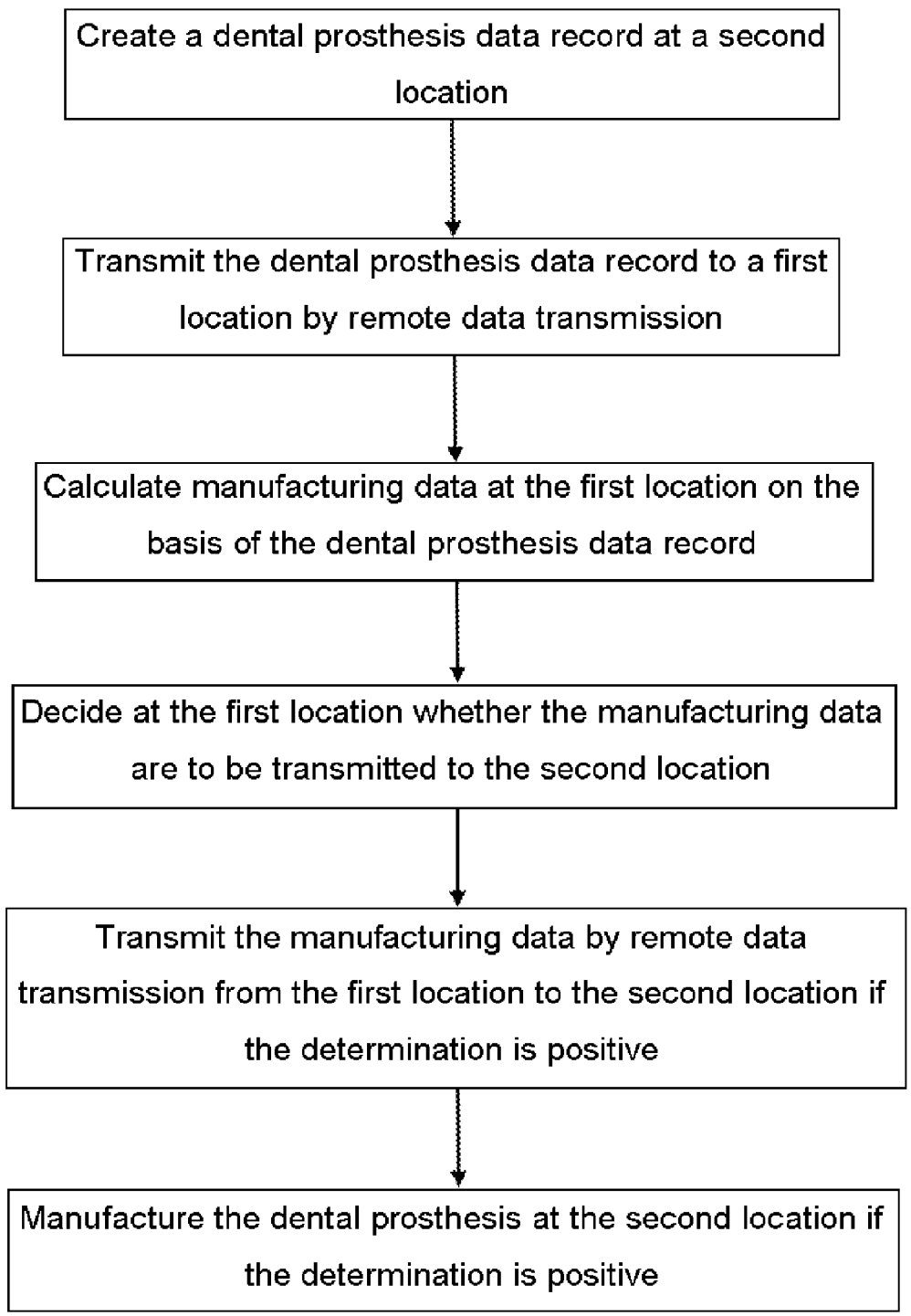
Figure 23:
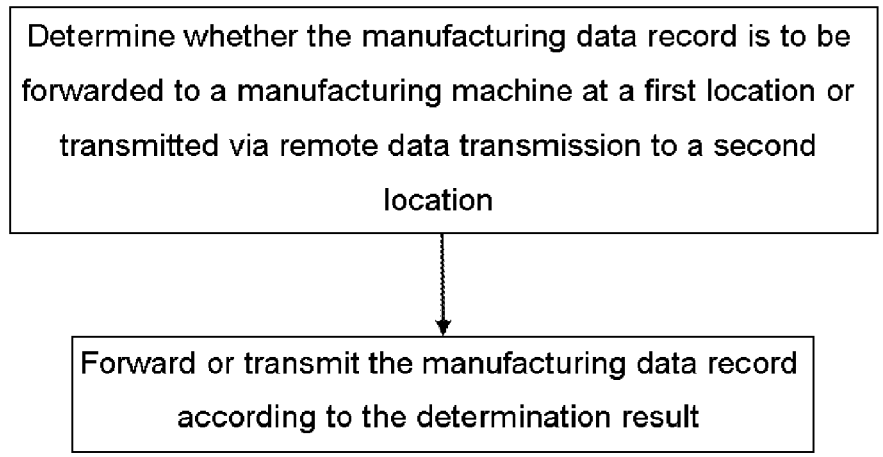
Figure 24:
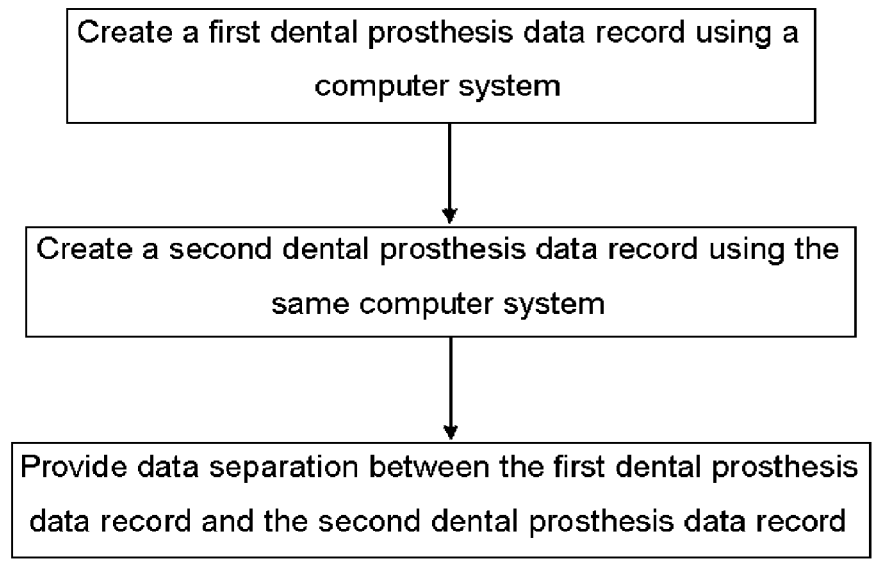
Figure 25:
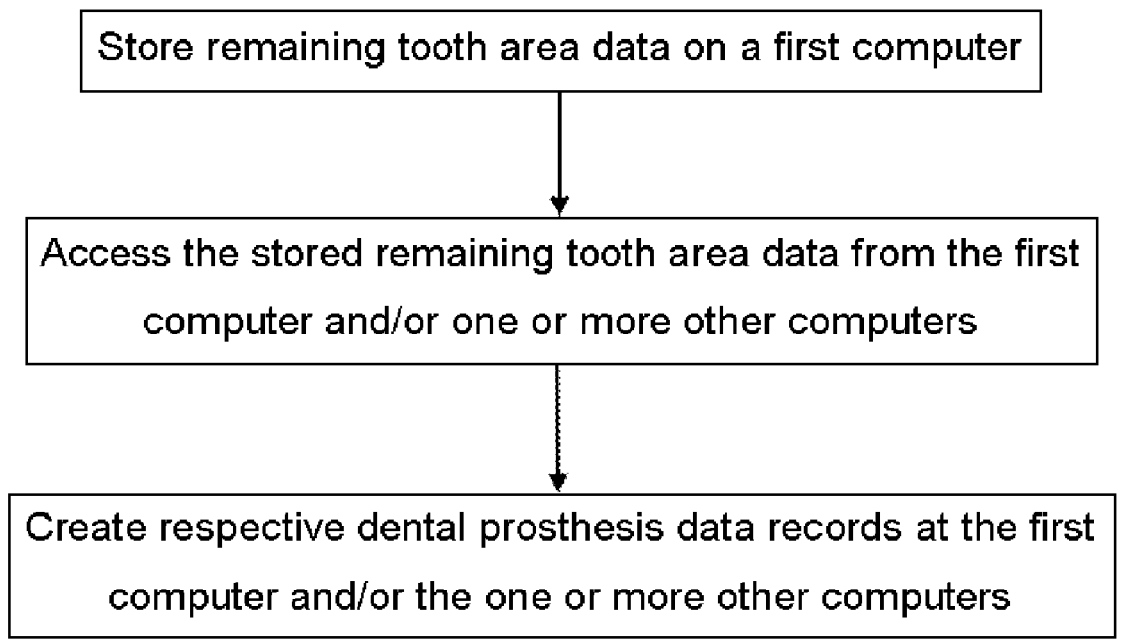

FIG. 6 shows two remote locations (A) and (B). Location (A) is, for example, that of a dentistry laboratory, and location (B) that of a production center and/or computer center. At location (B), a system for calculating milling data 24 is installed which can calculate the milling data for the control of a milling machine 26, 30 from a dental prosthesis data record. The milling machine 26 can mill a dental prosthesis out of a blank 28 with a cutter head 27. Equally, the milling machine 30 can mill a dental prosthesis out of a blank 32 with the cutter head 31. Instead of the milling machine 26 and/or the milling machine 30, other machines for manufacturing dental prostheses can also be provided. Correspondingly, instead of or in addition to the system for calculating milling data, a corresponding system for calculating manufacturing data has to be provided.

From the system for calculating milling data 24, the milling data can be transmitted to location (A) by means of remote data transmission 25, so that they can be forwarded to the milling machine 26 installed there. The milling data can also be forwarded from the system for calculating milling data 24 to a milling machine 30 at the same location (B) (see 29). Whether the milling data are transmitted to the milling machine 26 or to the milling machine 30, can depend on various factors. On the one hand, it can be preset on the orderer's demand. However, one can also examine which manufacturing mode is more reasonable, quicker, cheaper or otherwise advantageous. The manufacture with the milling machine 26, for example, has the advantage that a dispatch of the dental prosthesis to the dentistry laboratory is not necessary. The manufacture in the production center (B), however, has the advantage that by large scale manufacture low costs can be achieved as a good utilization of the milling machine 30 can be ensured. Moreover, larger dental prostheses difficult to manufacture can be better manufactured with a more accurate and precise milling machine 23 provided with a larger working range.

The dental prosthesis data record from which the system for calculating milling data 24 calculates the milling data can either have been created at location (A) or at location (B), i. e. either by the dental laboratory technician or in the production center. It can be created all-automatically or semiautomatically by means of software. In FIG. 6, the case is shown where a dental prosthesis data record 22 was created at location (A) by the dental laboratory technician with a computer 21 and subsequently transmitted (23) to the production center at location (B). With the method, it is thus for example possible that a dental laboratory technician creates a dental prosthesis data record 22 with his computer 21, transmits the same by remote data transmission, such as, for example, via Internet (23) to the production center (B), where the system for calculating milling data 24 calculates the milling data and sends them back to location (A) by remote data transmission (25) where then the dental prosthesis can be manufactured with the milling machine 26.

In the production center (B), a central filing of the data in a corresponding memory 34 (see reference numeral 33) can also be performed. Here, the milling data record as well as the dental prosthesis data record can be filed.

It is also possible to transmit milling data to the milling machine 26 at the dental laboratory technician as well as to forward them to a milling machine 30 in the production center. In this case, for example, in the dentistry laboratory (A), a prototype of a dental prosthesis can be manufactured from a comparably soft material, which is inserted until the dental prosthesis of the production center (B) made of a harder material is manufactured and dispatched.

The represented milling machines can be triaxial milling machines (as symbolically indicated in the Figures). However, four-axial or five-axial milling machines can also be provided. Such appliances, however, are essentially more expensive, so that its employment rather offers itself in the production center (B).

One System <-> at Least Two Users

In a method for creating dental prosthesis data records, a user usually needs a computer with corresponding software which permits the modeling of dental prostheses. These computers are especially equipped for quick graphical data processing and are therefore technically rather complex. In order to offer a user the possibility of modeling dental prostheses with as little effort as possible, a method according to claim 37 and a system according to claim 38 are provided. Here, two users get the possibility of sharing one system, wherein, however, both users can keep their respective data separately from one another. To this end, advantageously an operating system of the computer is provided that permits separate data storage by several users (multi-user operating system). It is thus possible for two users to independently share one system. This can be interesting, for example, for two dental laboratories and/or dental practices which are situated close to one another and can share one system.

Data Server Modeling Client

In order to create dental prosthesis data records, one starts from digitalized data describing a remaining tooth area. Here, these data can be either obtained on the basis of models (usually from plaster) or directly at the remaining tooth area. For obtaining these data records, as a rule a corresponding scanner is provided which can scan remaining tooth areas or models. The scanner is as a rule connected to a computer which controls the scanner and stores or further processes, respectively, the scan data. The scanning is performed relatively quickly, i.e. within a period of down to less than a minute.

The modeling of a dental prosthesis is usually performed at the same computer as here the data and corresponding software for processing the data relevant for the dental prosthesis already exist. This modeling is largely computer-aided. However, this takes a relatively long time (compared to scanning). If the dental prosthesis is modeled, the next scanning operation for the next dental prosthesis can follow.

In contrast, there is the task of reducing the time for the creation of dental prosthesis data records or improving the utilization of the scanner and/or computer.

For doing so, a data server is provided on which scan data are collected and/or stored. This server can, for example, control a scanner by which scan data are collected. Then, however, one or more other computers (clients) are provided by which the dental prosthesis data records can be created (modeling). Meanwhile, however, the next scanning operation can be already executed, so that the data are then directly available for the next dental prosthesis data modeling when the previous modeling operation is completed. It is also possible to simultaneously model with several clients. Nevertheless, only one server is necessary as not much time is required for scanning. In case of many client computers, however, more than one server with scan data can also be provided in order to achieve higher capacities.

The server and the client or clients can be situated in the same dentistry laboratory and/or at the same dentist and/or production center. With this method or with such a system, it is, however, also possible that various dentists/laboratories/production centers share one system for obtaining scan data, and that they then, however, perform the modeling of the dental prostheses independently.

The invention claimed is:

1. Method, comprising:
    examining an initial dental prosthesis data record representing an initial dental prosthesis using finite element methods, after the initial dental prosthesis has been broken,
    automatically determining a change to the initial dental prosthesis data record according to results of the examination,
    producing a new dental prosthesis data record, wherein the new dental prosthesis data record automatically reflects the change to the initial dental prosthesis data record,
    examining the new dental prosthesis data record using finite element methods, and
    producing a new dental prosthesis corresponding to the new dental prosthesis data record.

2. Method according to claim 1, wherein examining the new dental prosthesis data record includes evaluating the breaking strength of the new dental prosthesis.

3. Method according to claim 2, wherein examining the new dental prosthesis data record includes considering data of a remaining tooth area onto which the new dental prosthesis is to be fitted and/or data of the tooth area opposite of the remaining tooth area.

4. Method according to claim 1, further comprising examining the stability of the new dental prosthesis during production.

5. Method according to claim 1, further comprising filing a result of examining the new dental prosthesis data record.

6. Method according to claim 1, wherein producing a new dental prosthesis corresponding to the new dental prosthesis data record is performed after examining the new dental prosthesis data record using finite element methods.

7. Method according to claim 6, further comprising producing and filing photographic pictures of the new dental prosthesis.

8. Method according to claim 1, wherein examining the new dental prosthesis data record using finite element methods is performed as part of a quality assurance process and/or part of a production process.

9. Method according to claim 1, further comprising graphically representing forces and/or pressures and/or tensions in the new dental prosthesis data record, in the form of colors or shades of gray.

10. Computer-readable medium storing instructions that, when executed by a computer, perform the method according to claim 1.

11. Computer program including program code means for performing the method of claim 1 when executed on a computer.

12. Method according to claim 1, wherein the change to the initial dental prosthesis data record includes an increase in a breaking strength of the dental prosthesis.

* * * * *